4,980,369 12/1990 Chandraratna ............... 549/23

United States Patent [19]

Chandraratna

[11] Patent Number: 5,053,523
[45] Date of Patent: Oct. 1, 1991

[54] ETHYNYL-CHROMAN COMPOUNDS

[75] Inventor: Roshantha A. S. Chandraratna, El Toro, Calif.

[73] Assignee: Allergan, Inc., Irvine, Calif.

[21] Appl. No.: 610,491

[22] Filed: Nov. 6, 1990

Related U.S. Application Data

[62] Division of Ser. No. 409,477, Sep. 19, 1989, Pat. No. 5,023,341.

[51] Int. Cl.$^5$ .......................... C07D 311/04
[52] U.S. Cl. .................................. 549/398
[58] Field of Search ................... 549/398, 406

[56] References Cited

U.S. PATENT DOCUMENTS 4,810,804  3/1989  Chandraratna ............... 549/398
4,900,476  2/1990  Chan et al. .................. 549/411

Primary Examiner—Jane T. Fan
Assistant Examiner—Raymond Covington
Attorney, Agent, or Firm—Gabor L. Szekeres; Robert J. Baran; Martin A. Voet

[57] ABSTRACT

6-Ethynyl-chroman derivatives wherein $R_1$, $R_2$, $R_3$, $R_4$, and $R_5$, hydrogen or lower alkyl groups of one to six carbons wherein $R_1$, $R_2$, $R_3$, $R_4$, and $R_5$ may be identical or different from one another, X is oxygen, and Z is hydrogen of the following formula:

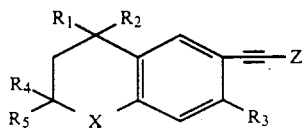

9 Claims, No Drawings

ETHYNYL-CHROMAN COMPOUNDS

BACKGROUND OF THE INVENTION

1. Cross-reference to Related Application

The present application is a divisional of application Ser. No. 409,477, filed on Sept. 19, 1989, expected to be issued as U.S. Pat. No. 5,023,341.

2. Field of the Invention

The present invention is directed to the preparation of compounds which have retinoic acid-like biological activity. More specifically, the present invention is directed to processes and intermediates which result in the synthesis of disubstituted acetylene compounds having retinoic acid-like activity

3. Related Art

European Patent Application 176034A (published Apr. 2, 1986) discloses tetrahydronaphtalene compounds having an ethynylbenzoic group. U.S. Pat. No. 4,739,098 discloses compounds wherein three olefinic units from the acid-containing moiety of retinoic acid are replaced by an ethynyphenyl functionality. These compound have retinoic acid-like biological activity.

U.S. Pat. No. 4,810,804 (issued on March 7, 1989) based on an application of the same inventor and assigned to the same assignee as the present application, discloses such disubstituted acetylene compounds wherein one of the substituents of the acetylene (ethyne) group is a substituted phenyl group, and the second substituent is a substituted or unsubstituted chromanyl, thiochromanyl or tetrahydroquinolinyl group. The compounds disclosed and claimed in U.S. Pat. No. 4,810,804 have retinoic acid-like biological activity.

Several co-pending applications of the present inventor, which applications are assigned to the assignee of the present application, are directed to further types of disubstituted acetylene compounds wherein one substituent of the acetylene (ethyne) moiety is a substituted phenyl or a substituted heteroaryl group, and the other substituent is a substituted or unsubstituted chromanyl, thiochromanyl or tetrahydroquinolinyl group. The disubstituted acetylene compounds described and claimed in the aforesaid co-pending applications have significant retinoic acid-like activity.

Retinoic acid-like activity has been generally recognized in the art to be associated with useful biological activity. Specifically, compounds having retinoic acid-like activity are useful as regulators of cell proliferation, and particularly as agents for treating dermatoses, such as acne, Darier's disease, psoriasis, icthyosis, eczema, atopic dermatitis and epithelial cancers, for treating arthritic diseases and other immunological disorders (e.g. lupus erythematosus) for promoting wound healing, for treating dry eye syndrome and for reversing the effects of sun damage to skin.

With respect to the synthetic processes of the present invention which involve either the formation of an acetylenic (ethynyl) function in the compounds of the invention, or the coupling of the compounds of the invention which already have the ethynyl function, with a halogen substituted phenyl or heteroaryl group, the following articles comprise background information: A General Synthesis of Terminal and Internal Arylalkynes by the Palladium-Catalyzed Reaction of Alkynylzinc Reagents with Aryl Halides by Anthony O. King and Ei-ichi Negishi, *J. Org. Chem.* 43 1978 p 358; Conversion of Methyl Ketones into Terminal Acetylenes and (E)-Trisubstituted olefins of Terpenoid Origin by Ei-ichi, Anthony O. King, and William L. Klima, *J. Org. Chem.* 45 1980 p. 2526, and A Convenient Synthesis of Ethynylarenes and Diethynylarenes by S. Takahashi, Y. Kuroyama, K. Sonogashira, N. Hagihara, *Synthesis* 1980 p 627–630.

SUMMARY OF THE INVENTION

The present invention is directed to a novel process for making the biologically active and useful disubstituted acetylene compounds having as one of the substituents a substituted or unsubstituted chromanyl, thiochromanyl or tetrahydroquinolinyl group. In another aspect, the present invention covers intermediate compounds which are utilized in the process to make the aforementioned biologically active disubstituted acetylenes.

Specifically, in accordance with the present invention the 6-thiochromanyl-ethyne, 6-chromanyl-ethyne and 6-tetrahydroquinolinyl-ethyne compounds of Formula 1, or their suitable metal salts are reacted with a suitable halogensubstituted phenyl or heteroaryl compound of Formula 2 to provide the compounds of Formula 3. The compounds of Formula 3 either have useful retinoic acid-like activity or are readily converted by routine organic synthetic steps (such as esterification, deesterification, homologation, oxidation, reduction, amide formation or the like) to compounds having the retinoic acid-like activity. (Formulae 1, 2 and 3 are incorporated in Reaction Scheme 1).

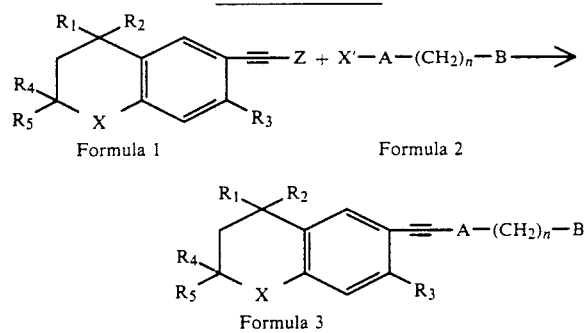

Reaction Scheme 1

In Formulae 1, 2, and 3, $R_1$, $R_2$, $R_3$, $R_4$ and $R_5$ are hydrogen or lower alkyl groups (of 1–6 carbons) where $R_1$, $R_2$, $R_3$, $R_4$ and $R_5$ may be identical or different from one another) X is S, O or NR' where R' is hydrogen or lower alkyl, Z represents hydrogen or a metal ion capable of forming a salt with the ethynyl moiety of the molecule, X' is a leaving group such as a halogeno group, A is phenyl, or heteroaryl such as pyridinyl, thienyl, furyl, pyridazinyl, pyrimidinyl, pyrazinyl, thiazolyl or oxazolyl, n is an integer between 0 to 5, and B is H, —COOH or a pharmaceutically acceptable salt, ester or amide thereof, —CH$_2$OH or an ether or ester derivative, or —CHO or an acetal derivative, or —COR$_1$ or a ketal derivative where $R_1$ is an alkyl, cycloalkyl or alkenyl group containing 1 to 5 carbons.

The reaction shown in Reaction Scheme 1, i.e. the coupling between the compounds of Formula 1 and the compounds of Formula 2, is conducted, in accordance with the invention in the presence of cuprous iodide and in the further presence of Pd(PQ$_3$)$_2$Cl$_2$ (Q is phenyl) or similar complex when Z is hydrogen, and in the presence of Pd(PQ$_3$)$_4$ (Q is phenyl) or similar complex when Z is a metal ion, such as ZnCl$^+$.

The compounds set forth in Formula 1, comprise another aspect of the present invention. These compounds are useful as intermediates for the synthesis of the biologically active and useful retinoic acid-like compounds of Formula 3.

When the preferred compounds of Formula 1 are reacted with compounds of Formula 2, then, in the resulting compounds of Formula 3 the X, R$_1$, R$_2$, R$_3$, R$_4$ and R$_5$ substituents are defined as for Compounds 1 through 9.

The reaction conditions for the coupling of compounds of Formula 1 with the compounds of Formula 2, in accordance with the present invention, as well as the processes for synthesizing the compounds of Formula 1, are explained in the ensuing description of Specific Embodoments and examples.

GENERAL EMBODIMENTS

Definitions

The term "ester" as used here refers to and covers any compound falling within the definition of that term as classically used in organic chemistry. Where B (of Formulae 1 and 2) is —COOH, this term covers the products derived from treatment of this function with alcohols. Where the ester is derived from compounds where B is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbons atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1-6 carbon atoms. Also preferred are the phenyl or lower alkylphenyl esters.

Amide has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2-5 carbon atoms, straight chain or branched.

A pharmaceutically acceptable salt may be prepared for any compound made in accordance with this invention, provided the compound has a functionality capable of forming such salt, for example an acid or an amine functionality. A pharmaceutically acceptable salt may be any salt which retains the activity o parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds which are preferably utilized in the synthetic process of the present invention to introduce the substituted chromanyl, substituted thiochromanyl, and substituted tetrahydroquinolinyl moiety as one of the substituents of the ethyne portion of the biologically active compounds, and which therefore are the preferred intermediates in accordance with the invention, are shown in Formula 4.

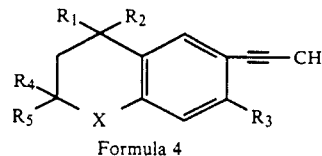

Formula 4

These preferred compounds and intermediates are:
Compound 1 X=S; R$_1$=R$_2$=CH$_3$ R$_3$=R$_4$=R$_5$=H
Compound 2 X=S; R$_1$=R$_2$=R$_3$=CH$_3$ R$_4$=R$_5$=H
Compound 3 X=S R$_1$=R$_2$=R$_4$=R$_5$=CH$_3$ R$_3$=H
Compound 4 X=O R$_1$=R$_2$=CH$_3$ R$_3$=R$_4$=R$_5$=H
Compound 5 X=O R$_1$=R$_2$=R$_4$=R$_5$=CH$_3$ R$_3$=H
Compound 6 X=NH R$_1$=R$_2$=CH$_3$ R$_3$=R$_4$=R$_5$=H
Compound 7 X=NH R$_1$=R$_2$=R$_4$=R$_5$=CH$_3$ R$_3$=H
Compound 8 X=S R$_1$=R$_2$=R$_3$=R$_4$=R$_5$=CH$_3$
Compound 9 X=O R$_1$=R$_2$=R$_3$=R$_4$=R$_5$=CH$_3$ 4,4-dimethyl-6-ethynylthiochroman (Compound 1)
4,4,7-trimethyl-6-ethynylthiochroman (Compound 2)
2,2,4,4-tetramethyl-6-ethynylthiochroman (Compound 3)
4,4-dimethyl-6-ethynylchroman (Compound 4)
2,2,4,4-tetramethyl-6-ethynylchroman (Compound 5)
4,4-dimethyl-6-ethynyl-1,2,3,4-tetrahydroquinoline (Compound 6)
2,2,4,4-tetramethyl-6-ethynyl-1,2,3,4-tetrahydroquinoline (Compound 7)
2,2,4,4,7-pentamethyl-6-ethynylthiochroman (Compound 8)
2,2,4,4,7-pentamethyl-6-ethynylchroman (Compound 9)

The metal (preferably zinc) salts of the preferred compounds are also preferred as intermediates in the process of the invention.

Generally speaking the compounds of Formula 1, or their metal (such as zinc) salts preferably the compounds of Formula 4 (or their salts), are reacted with the compounds of Formula 2 to provide the compounds of Formula 3.

When the preferred compounds of Formula 4 are reacted with compounds of Formula 2, then, in the resulting compounds of Formula 3 the X, R$_1$, R$_2$, R$_3$, R$_4$ and R$_5$ substituents are defined as for Compounds 1 through 9.

The reaction conditions for the coupling of compounds of Formula 1 with the compounds of Formula 2, in accordance with the present invention as well as the processes for synthesizing the compounds of Formula 1, are explained in the ensuing description of Specific Embodiments and Examples.

With respect to biological activity of the compounds of Formula 3 made in accordance with the process of the present invention (utilizing the intermediates of the invention in the process) the following is noted.

The retionic acid like activity of these compounds was confirmed through the classic measure of retionic acid activity involving the effects of retionic acid on ornithine decarboxylase. The original work on the correlation between retionic acid and decrease in cell proliferation was done by Verma & Boutwell, Cancer Research, 1977, 37, 2196-2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoylphorbol-13-acetate (TPA) induces ODC activity. Retionic acid inhibits this induction of ODC activity by TPA. The compounds of this invention also inhibit TPA induction of ODC as demonstrated by an assay essentially following the procedure set out in Cancer Res., 35, 1662-1670, 1975.

By way of example of retionic acid-like activity it is noted that in the assay conducted essentially in accordance with the method of Verman & Boutwell, ibid, the following examples of compounds made in accordance with the process of the present invention (Compounds 10, 11 and 12) attained an 80% inhibition of TPA induced ODC activity at the following concentrations ($IC_{80}$):

| Compound | $IC_{80}$ conc (mmols) |
| --- | --- |
| 10 | 0.69 |
| 11 | 0.13 |
| 12 | 0.2 |

Compounds 10, 11 and 12 are characterized with reference to Formula 3 as follows:

Compound 10 $X=S$ $R_1=R_2=R_4=R_5=CH_3$ $R_3=H$, $A-(CH_2)_n-B=$ethyl 6-nicotinate Compound 11 $X=O$ $R_1=R_2=R_4=R_5=CH_3$ $R_3=H$ $A-(CH_2)_n-B=$ethyl 6-nicotinate.

Compound 12 $X=O$ $R_1=R_2=R_3=R_4=R_5=CH_3$ $A-(CH_2)_n-B=$ethyl 6-nicotinate.

In view of their retinoic acid-like activity the compounds of Formula 3 may be administered systematically or topically for treatment of a variety of conditions, as is indicated in the introductory section of the present application for patent. For a detailed description of the modes of administration, of various pharmaceutical formulations and dosages in the treatment of mammals (including humans) with the compounds of Formula 3, reference is made to U.S. Pat. No. 4,810,804, the specification of which is incorporated herein by reference.

SPECIFIC EMBODIMENTS

The compounds of the invention which are defined in Formula 1, and which serve as key intermediates in the process steps of the invention to make the compounds of Formula 3, can be made by a number of different synthetic chemical pathways. To illustrate this invention, there is here outlined a series of steps which have been proven to provide the compounds of Formulae 1 and 3 when such synthesis is followed in fact and in spirit. The synthetic chemist will readily appreciate that the conditions set out here are specific embodiments which can be generalized to any and all of the compounds represented by Formulae 1 and 3. Furthermore, the synthetic chemist will readily appreciate that the herein described synthetic steps may be varied and or adjusted by those skilled in the art without departing from the scope and spirit of the invention. Moreover, it should be understood that some of the steps and processes utilized in the hereinbelow given examples of the compounds of Formula 1, are novel and innovative on their own right. Such novel steps are described here in sufficient detail to enable the ordinary artisan to duplicate such steps.

With reference to the compounds of Formula 1, Reaction Scheme 2 illustrates an example of their synthesis when $X=S$ and $R_4$ and $R_5$ are both hydrogen.

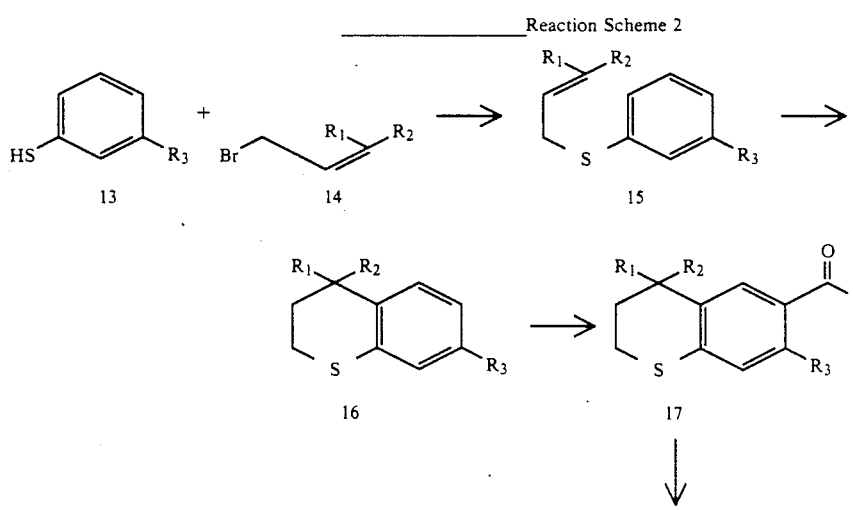

-continued
Reaction Scheme 2

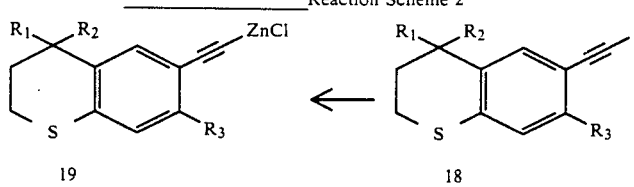

Thus, with reference to Reaction Scheme 2, a thiophenol 13 which may be substituted with the $R_3$ substituent (defined above as hydrogen or lower alkyl) in the 3 position is alkylated, preferably under strongly basic conditions such as NaOH in a polar solvent (acetone, room temp.) with the Compound 14, which is either 1-bromo-3-methyl 2-butene ($R_1$ and $R_2$ are methyl, available from Aldrich) or a derivative thereof where either $R_1$ and $R_2$ or both are lower alkyl other than methyl. The resulting alkylated thiophenol (sulfide, Compound 15) is thereafter ring closed under Fridel Crafts or like conditions, typically by refluxing in a inert solvent such as benzene or toluene, in the presence of phosphorous pentoxide and phosphoric acid. The resulting thiochroman 16, made in accordance with Reaction scheme 2, has no substituents in the 2 position, and preferably in accordance With this reaction scheme $R_1$ and $R_2$ are methyl and $R_3$ is hydrogen.

Compound 16 is acetylated under Fridel Crafts conditions, or the like, preferably with acetyl chloride (AlCl$_3$, CH$_2$Cl$_2$, reflux) to provide the 6-acetyl-thiochroman 17. The acetyl function of Compound 17 is converted into an acetylenic (ethynyl) function by means of lithium diisopropylamide, or a similar base, at reduced temperature. An intermediate derived from Compound 17 (presumably a lithium salt of the corresponding enol, not shown on Reaction Scheme 2) is esterified by treatment with diethychlorophosphate (or the like ) and is again reacted at reduced temperature (e.g. $-78$ degrees C.) with lithium diisopropylamide, to form the triple bond (presumably by an elimination reaction) and to yield the 6-ethynylthiochroman derivative (Compound 18).

It is noted at this point that the present invention is not intended to be limited or bound by the above-mentioned and other theories of reaction mechanisms. Brief description of theory of reaction mechanisms (where applicable) are given to further enable and facilitate the work of a skilled artisan in the field to modify and adjust the synthetic conditions to fit particular specific intermediates and to make the several compounds of the invention, without departing from the scope and spirit of the invention.

The 6-ethynyl-thiochroman 18 is either utilized directly in the coupling reaction indicated in Reaction Scheme 1, or is converted to a metal (zinc) salt (Compound 19) before the coupling step.

Generally speaking the zinc chloride salts (Compounds 19) are prepared under conditions which exclude water and oxygen. A dry, ether-type solvent such as dialkyl ether or a cyclic ether such as a furan or pyran, particularly a tetrahydrofuran, may be used as the solvent. A solution of Compound 18 is first prepared under an inert atmosphere (argon or nitrogen) and then a strong base such as n-butyl lithium is added (in about a 10% molar excess). This reaction is begun at a reduced temperature of between $-10$ degrees and $+10$ degrees C., preferably about 0 degrees C. The reaction mixture is stirred for a short period, between 30 minutes and 2 hours, and then treated with about a 10% molar excess of fused zinc chloride dissolved in the reaction solvent. This mixture is stirred for an additional 1-3 hours at about the starting temperature, then the temperature is increased to about ambient temperature for 10-40 minutes.

The foregoing general description for the preparation of the Zncl salts symbolized by Compound 19, are also applicable, with such modifications which will be readily apparent to the skilled artisan in the field, to the preparation of all Zncl salts corresponding to Formula 1.

Reaction Scheme 3 shows another method for preparing the compounds of Formula 1 when $X=S$ and $R_4$ and $R_5$ are hydrogen. The synthetic sequence shown in Reaction Scheme 3 is preferably (but not exclusively) used when $R_3$ is not hydrogen. In contrast the reactions shown in Reaction scheme 2 are preferably (but not exclusively) used when $R_3$ is hydrogen.

Thus, with reference to Reaction Scheme 3 the 4-bromothiophenol (Compound 20) (which is preferably alkyl substituted in the 3-position) is alkylated with Compound 14. The resulting 4-bromo phenyl sulfides 21 are ring closed under conditions analogous to the ring closure of Compounds 15 described in connection with Reaction Scheme 2.

Reaction Scheme 3

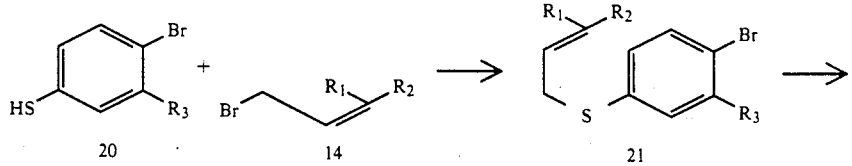

-continued
Reaction Scheme 3

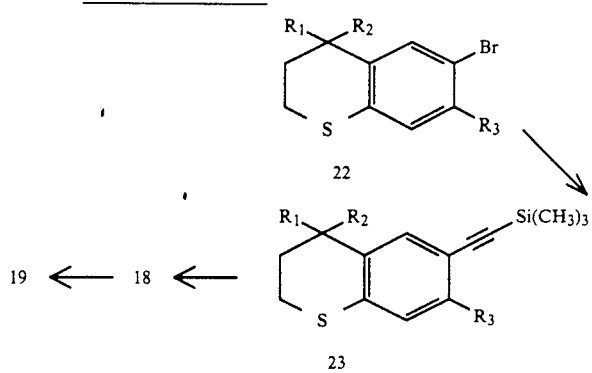

To introduce the acetylene (ethyne) portion into the molecule, the substituted 6-bromothiochroman 22 is reacted with trimethylsilylacetylene in the presence of cuprous iodide and a suitable catalyst, typically having the formula $Pd(PQ_3)_2Cl_2$ (Q is phenyl). The reaction is typically conducted in the presence of bis)triphenylphosphine) palladium (II) chloride catalyst, an acid acceptor, (such as triethylamine) under an inert gas (argon) atmosphere, by heating in a sealed tube. The resulting 6-trimethylsilylethynylthiochroman, is shown as Compound 23 in Reaction Scheme 3.

As is further shown on Reaction Scheme 3, the trimethylsilyl moiety is removed from the 6 -trimethylsilylethynyl-thiochromanyl-thiochroman 23 in the next synthetic step, to provide the ring substituted 6-ethynyl-thiochroman derivative (compound 18). The latter reaction is conducted under basic conditions, preferably under an inert gas atmosphere.

The 6-ethynyl-thiochroman 18 can be utilized directly in the coupling reaction set forth in Reaction Scheme 1, or prior to coupling can be converted to the corresponding ZnCl salt, as is described above.

Reaction Scheme 4 shows preparation of the compounds corresponding to Formula 1 where $X=S$ and at least one of the $R_4$ and $R_5$ groups is lower alkyl, preferably where $R_4$ and $R_5$ are both lower alkyl, and still more preferably where $R_4$ and $R_5$ are identical with one another.

Thus, with specific reference to Reaction scheme 4, the 2 substituted (preferably 2,2 di-substituted) 6-ethynyl thiochromans can be prepared as follows. The 4-bromo-thio-phenol (Compound 20) is acylated with an acylating agent such as an acid chloride (Compound 24) derived from an appropriately substituted acrylic acid. The acylation is conducted in an inert solvent (such as tetrahydrofuran) in the presence of strong base (for example sodium hydride). The resulting thioester (Compound 25)

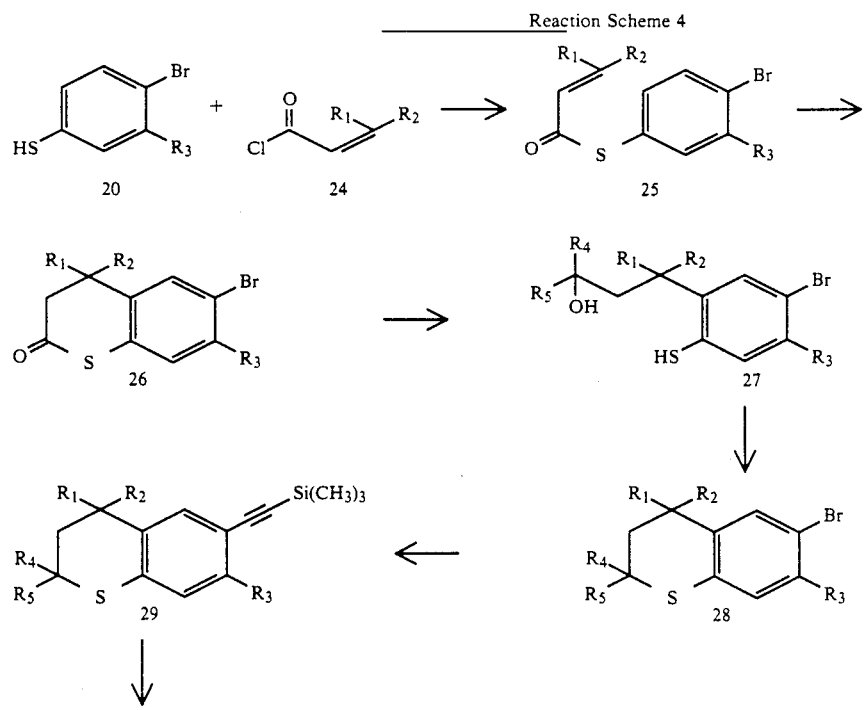

Reaction Scheme 4

-continued
Reaction Scheme 4

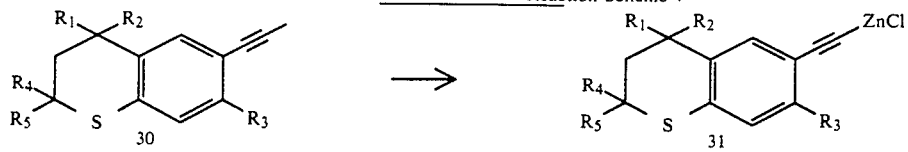

which contains the olefinic bond of the acrylic acid moiety is ring closed in the presence of a Friedel Crafts type catalyst (such as aluminum chloride) by stirring in a suitable solvent such as methylene chloride. The resulting 2-oxo-6-bromothiochromane (compound 26) is usually isolated in crystalline form.

The $R_4$ and/or $R_5$ substituents (both of which cannot be hydrogen when the steps of Reaction Scheme 4 are used) and which preferably are identical with one another (for example both are methyl) are introduced by treating the 2-oxo-6-bromothiochromane (Compound 26) with a Grignard reagent, bearing the alkyl substituents $R_4$ and $R_5$ (such as methylmagnesium bromide when $R_4$ and $R_5$ are methyl). It will be readily understood by those skilled in the art that depending on the relative molecular ratios of the Grignard reagent and of the oxothiochroman compound (Compound 26), and also depending on the reaction conditions, the primary products of the reaction may be derivatives where either one or two alkyl groups have been introduced through the Grignard reaction. When the Grignard reagent (such as methylmagnesium bromide) is in excess, the thiochromane ring is opened and the tertiary alcohol derivative of the 4-bromo thiophenol (Compound 27) is formed.

Ring closure of the thiophenol derivative (Compound 27) which has the desired $R_1$, $R_2$, $R_3$, $R_4$ and $R_5$ substituents, is affected by heating in acidic conditions, preferably by heating Compound 27 in aqueous acid. The resulting 6-bromothiochroman which bears the desired alkyl (or hydrogen) substituents, $R_1$, $R_2$, $R_3$, $R_4$ and $R_5$, is shown as Compound 28 in Reaction Scheme 4

The 6-bromothiochromans 28 (which differs from the 6-bromothiochromans 22 only in that in Compound 28 the 2 position of the thiochroman ring is substituted) is converted to the 6-(2-trimethylsilyl)-ethynyl derivative 29, and thereafter into the 6-ethynyl derivative 30, (and further if desired into the ZnCl salts 31) in reaction steps which are analogous to the corresponding steps described in connection with Reaction Scheme 3.

Turning now to compounds of Formula 1 where X=O and where $R_4$ and $R_5$ are H, (that is turning to chromans substituted in the 4, and possibly in the 7 position) the compounds can be made as indicated in Reaction Scheme 5.

Reaction Scheme 5

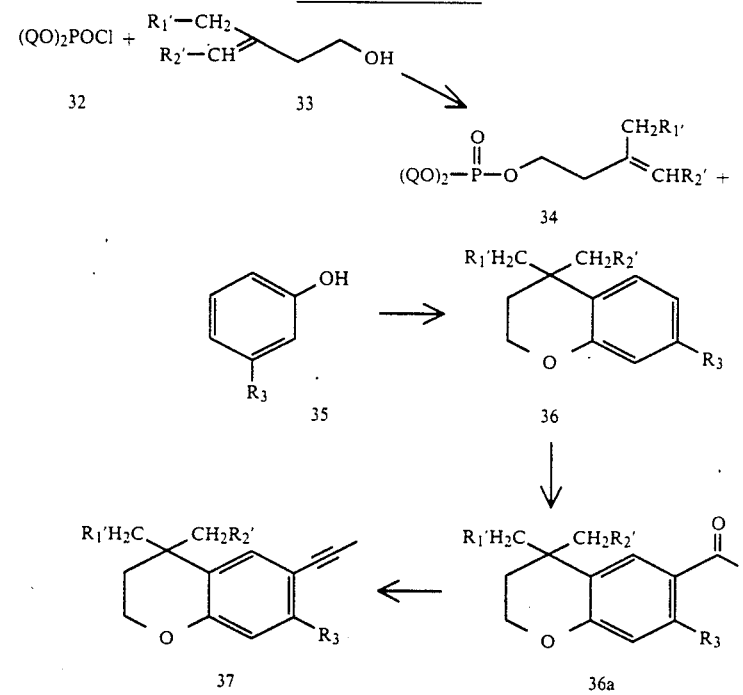

In Reaction Scheme 5 Q is phenyl and $R_1'$ and $R_2''$ are hydrogen or lower alkyl having 1 to 5 carbons, and $R_3$ is defined as above in connection with Formula 1. The reaction sequence is hereinafter further described for the preferred case where $R_1'$ and $R_2''$ and $R_3$ are all hydrogen, i.e. for the synthesis of 4,4-dimethyl-6-ethynylchroman (Compound 4).

With reference to Reaction Scheme 5, the phosphate (Compound 34) is prepared from the corresponding diphenyl chlorophosphate 32 and 3-methyl 3-butene-1-ol (Compound 33, $R_1'$ and $R_2''$ are both H) available from Aldrich, or prepared by means known in the art. It is preferred to prepare Compound 34 by dissolving the alcohol 33 in about a 10% excess of pyridine or the like under an inert atmosphere cooled to approximately −10 degrees to 10 degrees C. This solution is then added drop-wise, under an inert atmosphere, to a solution of diphenyl chlorophosphate 32, in about an equal amount of the reaction solvent. About a 2-5% molar excess of diphenyl chlorophosphate 22 relative to the alcohol 33 is employed The atmosphere may be argon, nitrogen, or another inert gas. The mixture is heated at reflux for between 1 and 5 hours, preferably about 3, to effect the reaction. The product is then recovered by conventional means. The diphenyl phosphate ester (compound 34) is then reacted with a phenol 35 to effect formation of chroman (compound 36). For example, phenol 35 (or $R_3$ substituted phenol) is added to a flask already containing stannic chloride under argon which ter the acetyl group is converted to the ethynyl group through treatment with lithium diisopropylamide, dialkyl chlorophosphate and another treatment with lithium diisopropylamide.

Compound 4 (or its analogs where $R_3$ is lower alkyl and/or where the 2,2 substituents have 2-6 carbons) can also be converted to the corresponding ZnCl salt (not shown in Reaction Scheme 5) prior to a coupling reaction with compounds of Formula 2.

Reaction Scheme 6 discloses, in general terms, the preparation of compounds of Formula 1 where X=O and $R_4$ and $R_5$ both are not hydrogen. In other words Reaction Scheme 6 discloses the preparation of 2 substituted, and preferably of 2,2-disubstituted 6-ethynyl chromanes.

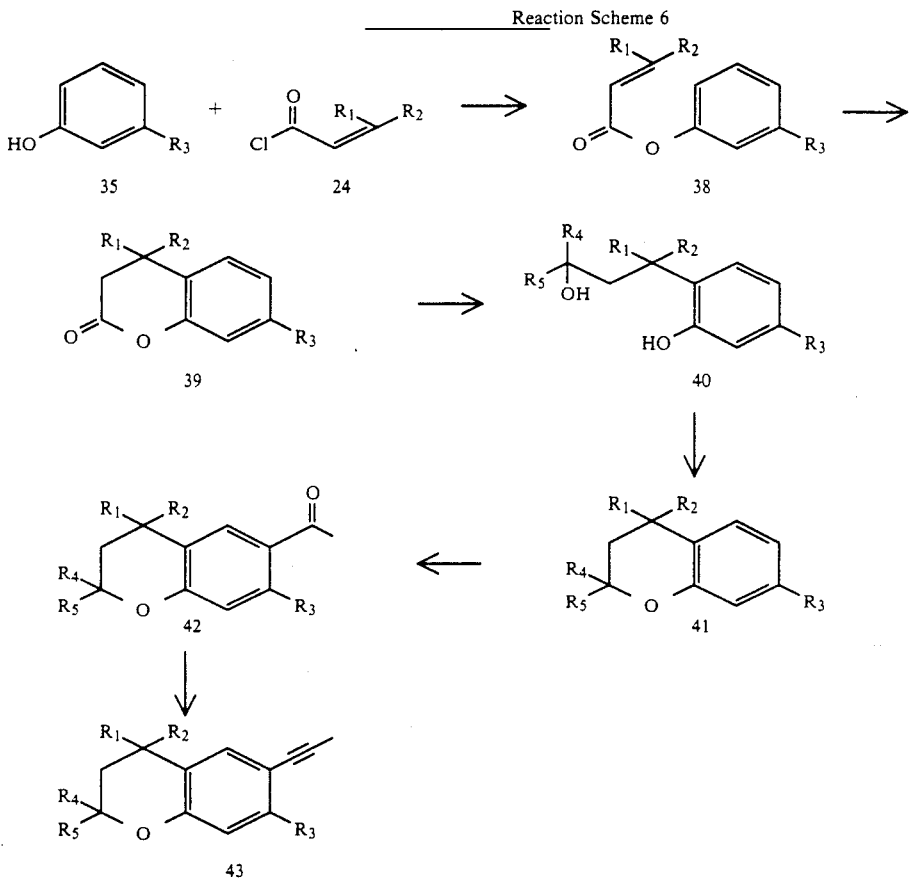

Reaction Scheme 6 has been cooled to between −10 degrees to 10 degrees C. After thorough mixing of this combination for about 15 minutes to an hour at the reduced temperature, the phosphate 34 is added at the reduced temperature. Both of these steps are carried out under an inert atmosphere such as argon or nitrogen. When the addition of the phosphate 34 is completed, the mixture is stirred at about ambient temperature for up to 24 hours. Then the reaction is quenched with a dilute solution of aqueous alkali metal base or the like. The product is recovered by extraction and other conventional means.

The acetylenic (ethynyl) function is introduced into the 4,4-disubstituted (and optionaly 7-substituted) chroman Compound 36 in a sequence of reaction steps which are described in Reaction scheme 2 in connection with the analogous thiochroman compounds. Thus, a 6-acetylated chromane (Compound 36a) is first obtained, by acetylation with acetyl chloride, and thereaf- Thus, in accordance with Reaction Scheme 6, phenyl, or a phenol substituted in the 3 (meta) position by an alkyl substituent ($R_3$) (Compound 35) is acylated with an acylating agent, such as the acid chloride (Compound 24)·derived from an appropriately substituted acrylic acid. In Reaction Scheme 6, just as in Reaction Scheme 4, the $R_1$ and $R_2$ substituents of the target compounds are introduced through this acrylic acid derivative 24. The acylation with the acid chloride 24 is preferably conducted in the presence of a strong base (e.g. sodium hydride) in an inert solvent (such as tetrahydrofuran). The resulting substituted phenyl-acrylate is shown in Reaction Scheme 6 as Compound 38.

The substituted phenyl-acrylate 3is ring closed under Friedel Crafts type reaction conditions (AlCl₃ catalyst, in an inert solvent, such as methylene chloride) to provide the 2-oxo-chroman compound (Compound 39)

which bears, in the 4-position, the $R_1$ and $R_2$ substituents and in the 6-position the $R_3$ substituent (as applicable). Just like the analogous 2-oxo-thiochroman 26 in Reaction Scheme 4, the 2-oxo-chroman 39 of Reaction Scheme 6 is treated with a Grignard reagent to introduce the $R_4$ and $R_5$ substituents. As it was noted out above, in this Reaction Scheme $R_4$ and $R_5$ both cannot be hydrogen, and in the preferred embodiments $R_4$ and $R_5$ are identical, for example both are methyl or ethyl.

Compounds of Formula 1 where X is NR' (R' is H or lower alkyl) and $R_4$ and $5_5$ are both hydrogen can be made in accordance with Reaction Scheme 7. The reaction sequence of Scheme 7 is hereinafter described, with primary emphasis to a preferred embodiment where R' is hydrogen, $R_1$ and $R_2$ (of Formula 1) are both methyl, and $R_3$ is hydrogen.

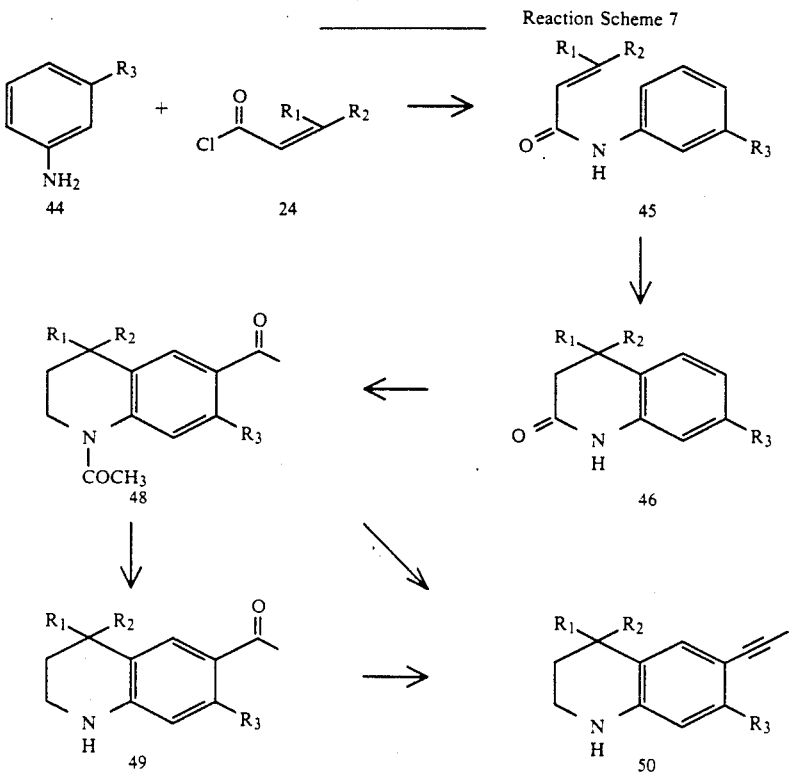

Reaction Scheme 7

When $R_4$ and $R_5$ are methyl, the Grignard reagent is preferably methylmagnesium chloride (dissolved in tetrahydrofuran, THF). A solution of Compound 39 in a suitable solvent, for example in dry diethylether is added to this Grignard reagent. The resulting phenol containing a tertiary alcohol side chain, (that is a molecule in which the chroman ring had been opened) is shown in Reaction Scheme 6 as Compound 40.

Compound 40 which already has the desired $R_1$, $R_2$, $R_3$, $R_4$ and $R_5$ substituents, is ring closed under acidic conditions, (e.g. by heating in aqueous sulfuric acid) to provide the chroman derivative (Compound 41). It should be noted that up to this point in the synthetic sequence similar or analogous steps are involved for making both the 2,2-disubstituted thiochroman (Reaction Scheme 4) and the 2,2-disubstituted chroman derivatives (Reaction Scheme 6), the only difference being that in Reaction Scheme 6 the starting phenol derivative does not have a halogen (such as a bromo) substituent.

As is further disclosed in Reaction Scheme 6, the ethynyl group is introduced into the 2-substituted (preferably 2,2-disubstituted) chroman in a sequence of steps which is analogous to the steps described in Reaction Scheme 2 for introducing the ethynyl function into 4-substituted thiochromans. 6-Ethynylchroman 43 can also be utilized directly in the coupling reaction with compounds of Formula 2, or can be converted to a suitable metal, preferably ZnCl, salt, in the manner described above.

Thus, with reference to Reaction Scheme 7, the tetrahydroquinoline moiety, that is where X is nitrogen, is made in part by the method described in European patent application No. 0130795 published Sept. 1, 1985 First, Compound 24, 3-methylcrotonoyl chloride (when $R_1$ and $R_2$ are both methyl) is reacted with aniline 44 to obtain the amide 45. This amide 45 is then cyclized using aluminum chloride in the absence of solvent to give Compound 46. Lithium aluminum hydride or another acceptable reducing agent of similar type is then used to reduce the 2-oxo-1,2,3,4-tetrahydroquinoline 46, preferably in inert solvent such as diethyl ether. The resulting amine 47 is then acetylated using acetyl chloride in a polar solvent such as pyridine followed by acetylation in the presence of aluminum chloride to give Compound 48. Compound 48 is then subjected to base hydrolysis to give the secondary amine 49.

The 6-acetyl group of Compound 49 is thereafter converted into an ethynyl group in the manner described above for analog transformation of 6-acetyl chromans or 6-acetyl thiochromans. The 6-ethynyl 1,2,3,4-tetrahydroquinoline (Compound 50) may be coupled directly or as the corresponding ZnCl salts, compounds of Formula 2.

Alternatively compounds of Formula I Where X=is NR', $R_4$ and $R_5$ are H, can also be prepared by the synthetic sequence outlined in Reaction Scheme 8 ($R_1$ and $R_2$ preferably are methyl). Reaction Scheme 8 will be self-explanatory to those skilled in the art in light of the analogous reactions disclosed in the present specification ($R_3$ is defined as above for Formula 1).

ethyl 5-(2-iodothien-5-yl)pentanoate;
ethyl 2-(3-chloropyridazin-6-yl) acetate;
ethyl 5-(3-chloropyridazin-6-yl)pentanoate;

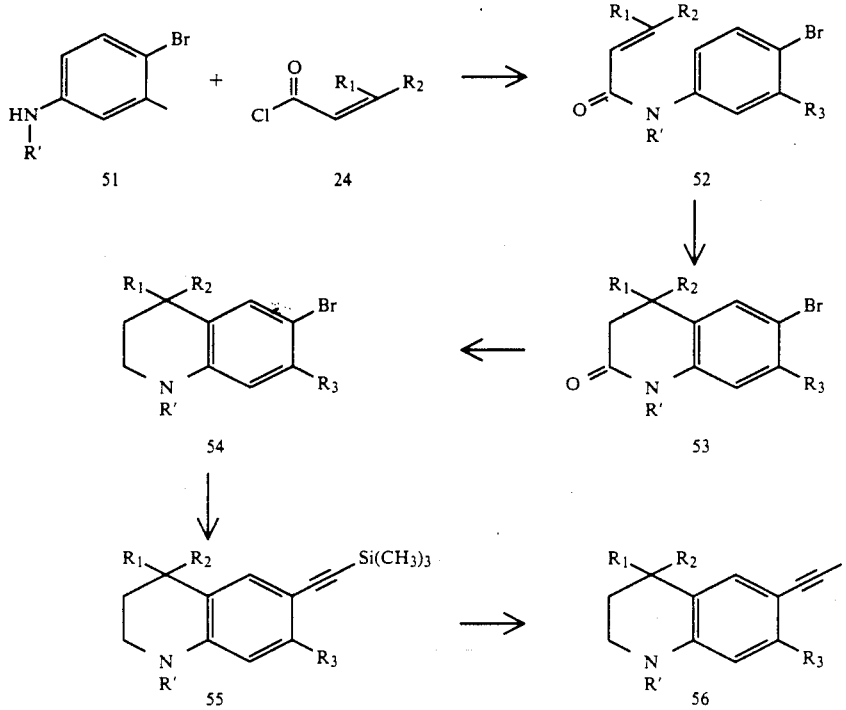

Reaction Scheme 8

The compounds of Formula 2 are coupled in accordance with the present invention with the compounds of Formula 1 to provide the biologically active compounds of Formula 3. The compounds of Formula 2 per se, are not new, and can be made in accordance with well known procedures, or by such adaptation of well known procedures which are within the skill of the practicing synthetic organic chemist.

In accordance with one preferred embodiment of the invention, group A of Formula 2 is a phenyl group, X' is halogen, preferably bromine or iodine. Ethyl4-iodobenzoate is one preferred example of a reagent in accordance with Formula 2, used in coupling with the compounds of Formula 1. Other examples, where A is phenyl, are: ethyl 4-iodophenylacetate, ethyl 4-iodophenylpropinoate, ethyl 4-iodo-phenylbutanoate, ethyl 4-iodo-phenylpentanoate. Reagents in accordance with Formula 2 where the X' and $(CH_2)_n$-B substituents respectively are in meta or ortho position on the phenyl ring, can also be used in the process of the invention. Moreover, the group characterized as B in Formula 2 may be a suitably protected or unprotected alcohol, aldehyde, ketone, amide, or such other functionality as is set forth in the definition of the Group B of Formula 2. The preparation of such compounds in accordance with Formula 2, suitable for coupling with compounds of Formula 1, will be within the skill of the practicing organic chemist in light of the present disclosure.

When group A of Formula 2 is heteroaryl then examples of preferred reagents are: ethyl 6-chloronicotinate, ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;

and the corresponding chloro, or other halo, substituted pyrimidinyl or pyrazinyl analogues of such esters. In this series also, the B grouping of the compound of Formula 2 can be protected unprotected alcohol, aldehyde, ketone, amide or other set forth in connection with Formula 2.

It is also within the scope of the present invention to couple compounds of Formula 1 with compounds of Formula 2, and thereafter subject the resulting molecule (particularly that portion thereof which is derived from the reagent of Formula 2) to such routine synthetic transformations as a blocking and deblocking, homologation, reduction or oxidation, ester formation, saponification, and the like, which results in the formation of further analogs within the scope of Formula 3 and having retinoic acid-like biological activity.

With respect to the novel coupling reaction of the process of the present invention, the following is noted. The coupling is affected typically in the presence of cuprous iodide, a suitable catalyst, typically of the formula $Pd(PQ_3)_2Cl_2$ and an acid acceptor, such as triethylamine, by heating in a sealed tube under an inert gas (argon) atmosphere.

Alternatively, the compound of Formula 1 is first converted to a salt (preferably ZnCl salt) for the coupling. An examplary generalized process for preparing ZnCl salts of the compounds of Formula 1 (where Z is converted from H to ZnCl) is described above in connection with Compounds 19.

Coupling of the Zncl salts of the 6-thiochromanyl, 6-chromanyl and 6-(1,2,3,4-tetrahydroquinolinyl)-ethyne compounds with compounds of Formula 2, is conducted in the of $Pd(PQ_3)_4$ catalyst (Q is phenyl). For further details of the conditions of these reactions, reference is made to the following detailed procedures which describe the preparation of specific compounds.

SPECIFIC EXAMPLES

Phenyl-3-methylbut-2-enylsulfide (Compound 60)

A mixture of 14.91 g (135.324 mmol) of thiophenol and 5.5 g (137.5 mmol) of NaOH in 100 ml acetone was heated at reflux for 2.5 hours and then treated dropwise with a solution of 20 g (134.19 mmol) of 1-bromo-3-methyl-2-butene in 20 ml acetone. This solution was refluxed for 40 hours and then stirred at room temperature for 24 hours. Solvent was then removed in vacuo and the residue was taken up in water and extracted with 3×50 ml ether. Ether extracts were combined and washed with 3×30 ml of 5% NaOH solution, then water, saturated NaCl solution and dried ($MgSO_4$). Solvent was then removed in vacuo and the residue further purified by Kugelrohr distillatin (80 degrees C., 0.75 mm) to give the title compound as a pale yellow oil. PMR ($CDCl_3$): & 1.57 (3H, s), 1.69 (3H, s), 3.52 (2H, d, J~7.7 Hz), 5.29 (1H, t, J~7.7 Hz), 7.14 (1H, t, J~7.0 Hz), 7.24 (2H, t, J~7.0 Hz), 7.32 (2H, d, J~7.0 Hz).

Proceeding in a similar manner, but substituting for thiophenol the appropriate 3-alkylthiophenol, the following compounds can be prepared:
3-methylphenyl-3-methylbut-2-enylsulfide;
3-ethylphenyl-3-methylbut-2-enylsulfide;
3-propylphenyl-3-methylbut-2-enylsulfide;
3-butylphenyl-3-methylbut-2-enylsulfide;
3-pentylphenyl-3-methylbut-2-enylsulfide; and
3-hexylphenyl-3-methylbut-2-enylsulfide.

4,4-Dimethylthiochroman (Compound 61)

To a solution of 15.48 g (86.824 mmol) of phenyl-3-methylbut-2-enylsulfide (Compound 60) in 160 ml benzene were added successively 12.6 g (88.767 mmol) of phosphorus pentoxide and 11 ml of 85% phosphoric acid. This solution was refluxed with vigorous stirring under argon for 20 hours, then cooled to room temperature. The supernatant organic layer was decanted and the syrupy residue extracted with 3×50ml ether. Organic fractions were combined and washed with water, saturated $NaHCO_3$ and saturated NaCl solutions and then dried ($MgSO_4$). Solvent was removed in vacuo and the residue purified by kugelrohr distillation (80 degrees C., 0.5 mm) to give the title compound as a pale yellow oil. PMR ($CDCl_3$): & 1.30 (6H, s), 1.90–1.95 (2H, m), 2.95–3.00 (2H, m), 6.96–7.00 (2H, m), 7.04–7.07 (1H, m), 7.30–7.33 (1H, m).

This method can be used to make 7-position alkyl analogues as exemplified by the following compounds:
4,4,7-trimethylthiochroman (Compound 2)
4,4-dimethyl-7-ethylthiochroman;
4,4-dimethyl-7-propylthiochroman;
4,4-dimethyl-7-butylthiochroman; and
4,4-dimethyl-7-hexylthiochroman.

4,4-Dimethyl-6-acetylthiochroman (Compound 62)

A solution of 14.3 g (80.21 mmol) of 4,4-dimethylthiochroman (Compound 61) and 6.76 g (86.12 mmol) of acetyl chloride in 65 ml benzene was cooled in an ice bath and treated dropwise with 26.712 g (102.54 mmol) of stannic chloride. The mixture was stirred at room temperature for 12 hours, then treated with 65 ml water and 33 ml conc. hydrogen chloride and heated at reflux for 0.5 hours. After being cooled to room temperature, the organic layer was separated and the aqueous layer extracted with 5×50 ml benzene. The recovered organic fractions were combined and washed with 5% sodium carbonate, water, saturated NaCl and then dried ($MgSO_4$). The solvent was removed in vacuo and the residue purified by flash chromatography (silica; 5% ethyl acetate in hexanes) followed by kugelrohr distillation (150 degrees C., 0.7 mm) to give the title compound as a pale yellow oil. PMR ($CDCl_3$): & 1.35 (6H, s), 1.92–1.98 (2H, m) 2.54 (3H, s), 3.02–3.08 (2H, m), 7.13 (1H, d, J~8.6 Hz), 7.58 (1H, dd, J~8.6 Hz, 2Hz), 7.99 (1H, d, J~2 Hz).

This procedure serves to acetylate all the compounds which can be made by the process given for the preparation of Compound 61.

4,4-Dimethyl-6-ethynylthiochroman (Compound 1)

To a solution of 1.441 g (14.2405 mmol) of diisopropylamine in 30 ml dry tetrahydrofuran under argon at −78 degrees C. was added dropwise 9 ml of 1.6M (14.4 mmol) n-butyl lithium in hexane. After stirring this solution at −78 degrees C. for 1 hour, it was treated dropwise with a solution of 2.95 g (13.389 mmol) of 4,4-dimethyl-6-acetyl-thiochroman (Compound 62) in 5 ml of dry tetrahydrofuran. After another hour of stirring at −78 degrees C., the solution was treated with 2.507 g (14.53 mmol) of diethyl chlorophosphate and brought to room temperature, where it was stirred for 3.75 hours. This solution was then transferred using a double ended needle to a solution of lithium diisopropylamide [prepared using 2.882 g (28.481 mmol) of diisopropylamine and 18 ml of 1.6M (28.8 mmol) n-butyllithium in hexane] in 60 ml dry tetrahydrofuran at −78 degrees C. The cooling bath was removed and the solution stirred at room temperature for 15 hours, then quenched with water and acidified to pH 1 with 3N hydrogen chloride. The mixture was extracted with 5×50 ml pentane and the combined organic fractions washed with 3N hydrogen chloride, water, saturated $NaHCO_3$ and saturated NaCl, then dried ($MgSO_4$). Solvent was then removed in vacuo, and the residue purified by kugelrohr distillation (100 degrees C., 0.7 mm) to give the title compound as a pale yellow solid. PMR ($CDCl_3$): & 1.34 (6H, s), 1.94–1.99 (2H, m), 3.04–3.08 (3H, m), 7.06 (1H, d, J~8.4 Hz), 7.17 (1H, dd, J~8.4 Hz, 2.1 Hz), 7.51 (1H, d, J~2.1 Hz).

Similarly, the acetyl group of all compounds prepared similar to the preparation of Compound 62, can be converted to an ethynyl function.

4,4-dimethyl-6-ethynylthiochroman ZnCl (Compound 63) and ethyl 4-(4,4-dimethylthiochroman-6-yl-ethynyl) benzoate (Compound 64)

Reaction vessels used in this procedure were flame dried under vacuum and all operations carried out in an oxygen-free, argon or nitrogen atmosphere. To a solution of 533.9 mg (2.6389 mmol) of 4,4-dimethyl-6-ethynyl-thiochroman (Compound 1) in 4 ml of dry tetrahydrofuran at 0 degrees C. was added dropwise 1.7 ml of 1.6M (2.72 mmol) n-butyl lithium in hexane. This was stirred at 0 degrees C. for 10 minutes and at room temperature for 15 minutes, cooled again to 0 degrees C. and then treated with a solution of 410 mg (3.005 mmol) of fused $ZnCl_2$ in 4 ml dry tetrahydrofuran using a double ended needle. Thereafter, the solution was stirred at 0 degrees C. for 45 minutes, then at room temperature for 20 minutes to give Compound 63. This product was not isolated but further used follows: A solution of 724.4 mg (2.6243 mmol) of ethyl 4-iodobenzoate iodobenzoate in 4 ml dry tetrahydrofuran was transferred by double ended needle into a suspension of 520 mg (0.45 mmol) of tetrastriphenylphosphine palladium in 5 ml dry tetrahydrofuran and stirred at room temperature for 20 minutes, then treated by double ended needle with the solution of the alkynyl zinc chloride prepared above. This mixture was stirred at room temperature for 18 hours, then quenched with ice and 30 ml 3N hydrogen chloride. Product was recovered by extraction with 3×75 ml ether. Ether fractions were combined and washed successively with saturated NaHCO$_3$ and saturated NaCl solutions and dried (MgSO$_4$). Solvent was removed in vacuo and the residue purified by flash chromatography (silica; 5% ethyl acetate in hexane) followed by HPLC (Whatman Partisil M-9 10/50; 4% ethyl acetate in hexane) to give ethyl (4,4-dimethylthiochroman-6-yl-ethynyl) benzoate (Compound 64) as a colorless oil. PMR (CDCl$_3$): & 1.36 (6H), 1.42 (3H, t, J~7 Hz), 1.93~1.99 (2H, m), 3.03–3.08 (2H, m), 4.40 (2H, q, J~7 Hz), 7.09 (1H, d, J~8.4 Hz), 7.22 (1H, dd, J~8.4 Hz, 2.1 Hz), 7.56 (1H, d, J~2.1 Hz), 7.59 (2H, d, J~7.8 Hz), 8.04 (2H, d, J~7.8 Hz).

(3-Methyl-4-bromo-phenyl)-3-methylbut-2-enylsulfide (Compound 65)

To a stirred solution of 9.52 g (68 mmol) of 3-methyl-4-bromo-thiophenol in 80 ml of acetone was added 2.86 g (68 mmol) of powdered sodium hydroxide and mixture stirred until dissolution was complete. The reaction mixture was then heated to reflux, and then treated with a solution of 11.26 g (68 mmol) of 4-bromo-2-methyl-2-butene in 20 ml of acetone. the mixture was heated at reflux for a further 0.5 h, cooled room temperature and the solvent removed in vacuo. The residue was taken up in 35 ml of water and extracted with ether. The ether extracts were combined and washed successively with water and saturated NaCl solution and then dried (MgSO$_4$). The solvent was removed in vacuo and the residue kugelrohr distilled (140–145 degrees C., 0.2 mm) to give the title compound as a colorless oil. PMR (CDCl$_3$): & 1.58 (3H, s), 1.70 (3H, s), 2.33 (3H, s), 3.49 (2H, d, J~7.8 Hz) 5.26 (1H, t, J~7.8 Hz), 6.98 (1H, dd, J~8.3 Hz, 2.3 Hz), 7.17 (1H, d, J~2.3 Hz), 7.38 (1H, d, J~8.3 Hz).

4,4,7-Trimethyl-6-bromothiochroman (Compound 66)

To 40 g of a vigorously stirred mixture of 10% phosphorous pentoxide in methane-sulfonic acid was added slowly 6.0 g (28.8 mmol) of (3-methyl-4-bromophenyl)-3-methylbut-2-enyl-sulfide (Compound 65). The mixture was stirred at room temperature for a further 2 h and was then poured onto ice. The mixture was extracted with 2×40 ml of ether and the combined ether extracts were washed successively with water and saturated NaCl solution and then dried. The solvent was removed in vacuo and the residue kugelrohr distilled (130 degrees C.; 0.07 mm) to give the title compound as a viscous oil. PMR (CDCl$_3$): & 1.28 (6H, s) 1.84–1.93 (2H, m), 2.26 (3H, s), 2.95–3.03 (2H, m), 6.94 (1H, s), 7.46 (1H, s).

4,4,7-Trimethyl-6-trimethylsilylethynyl-thiochroman (Compound 67)

A mixture of 624 mg (3.0 mmol) of 4,4,7-trimethyl-6-bromothiochroman (Compound 66) 314 mg (3.2 mmol) of trimethylsilyl acetylene, 40 mg (0.21 mmol) of cuprous iodide, 80 mg (0.11 mmol) of bis (triphenylphosphin) palladium (II) chloride and 1 ml of triethylamine was degassed under nitrogen and heated in a sealed tube at 85 degrees C. for 15 h. The mixture was then treated with a further 20 mg (0.11 mmol) of cuprous iodide and 40 mg (0.06 mmol) of the palladium (II) catalyst. The mixture was then heated under a nitrogen atmosphere in the sealed tube at 100 degrees C. for a further 64 h. The triethylamine was then removed under vacuum and the residue purified by flash chromatography (silica; hexanes) to give the title compound as a yellow oil. PMR (CDCl$_3$): & 0.28 (9H, s), 1.30 (6H, s), 1.88–1.97 (2H, m), 2.33 (3H, s), 2.97–3.05 (2H, m), 6.92 (1H, s), 7.43 (1H, s).

4,4,7-Trimethyl-6-ethynyl-Thiochroman (Compound 2)

A mixture of 380 mg (1.69 mmol) of trimethylsilyl (4,4,7-trimethyl-thiochroman-6-yl) ethyne, (Compound 67) 4 ml of isopropanol and 2.5 ml of aqueous 1N potassium hydroxide was degassed under nitrogen and stirred at room temperature for 16 h. The mixture was concentrated under vacuum and extracted with 2×10 ml of ether. The ether extracts were combined and washed successively with water and saturated NaCl solution and then dried (MgSO$_4$). The solvent was removed in vacuo to give title compound as a yellow oil. PMR (CDCl$_3$): & 1.31 (6H, s), 1.88–1.96 (2H, m), 2.35 (3H, s), 3.00–3.08 (2H, m), 3.25 (1H, s), 6.94 (1H, s), 7.47 (1H, s).

S-(4-bromopenyl) 3,3-dimethylthioacrylate (Compound 69)

To an ice bath cooled solution of 1.92 g (80 mmol) of NaH (obtained from a 60% suspension in mineral oil by 3×15 ml hexane wash) in 30 ml of dry THF was added slowly under argon a solution of 15.1 g (80 mmol) of 4-bromothiophenol in 60 ml of dry THF over 1 h. The mixture was stirred at 0 degrees C. for a further 30 min and then treated with a solution of 10.1 g (85 mmol) of dimethylacryloyl chloride in 30 ml of dry THF. The cooling bath was then removed and the mixture then stirred at room temperature for 40 h. The reaction mixture was poured into 200 ml of water containing 2 ml of glacial acetic acid and the organic layer was separated. The organic layer was washed with 2×75 ml of water and then dried (MgSO$_4$). The solvent was removed in vacuo to give the title compound as a yellow oil. PMR (CDCl$_3$): & 1.91 (3H, s), 2.14 (3H, s), 6.03–6.06 (1H, m), 7.28 (2H, d, J~8.6 Hz), 7.53 (2H, d, J~8.6 Hz).

4,4-Dimethyl-6-bromo-2-oxo-thiochroman (Compound 70)

To a stirred, ice-cooled suspension of 15.9 g (119 mmol) of aluminum chloride in 140 ml of methylene chloride was added under nitrogen, a solution of 21.64 g (79.9 mmol) of S-(4-bromophenyl) 3,3-dimethyl-thioacrylate (Compound 69) in 100 ml methylene chloride. The mixture was then stirred at room temperature for 72 h and then poured into 250 g of an ice and brine mixture. The mixture was extracted with methylene chloride and the combined organic extracts were washed with saturated NaCl solution and then dried (MgSO$_4$). The solvent was removed in vacuo and the residue recrystallized from hexanes to give the title compound as white crystals. PMR (CDCl$_3$): & 1.40 (6H, s), 2.67 (2H, s), 7.31–7.40 (3H, m). MS exact mass, m/e 269.9714 (calcd. for C$_{11}$H$_{11}$ SOBr, 269.9714).

4-Bromo-2-(1,1,3-trimethyl-3-hydroxybutyl) thiophenol (Compound 71)

To 3.49 g (32.8 mmol) of lithium perchlorate was added under argon 35 ml of 3.0M (105 mmol) methyl magnesium bromide in ether. The above mixture was treated dropwise with stirring with a solution of 2.961 g (10.926 mmol) of 4,4-dimethyl-6-bromo-2-oxo-thiochroman (Compound 70) and the reaction mixture was then heated at reflux for 70 h. The reaction mixture was then allowed to cool and poured onto a mixture of 100 g of ice and 8 ml of conc. $H_2SO_4$. The organic layer was separated and the aqueous layer was extracted with $2 \times 25$ ml of ether. The organic layers were combined and washed successively with $2 \times 25$ ml of saturated $NaHCO_3$ solution, 25 ml of water and 25 ml of saturated NaCl solution and then dried ($MgSO_4$). The solvent was removed in-vacuo and the residue purified by flash chromatography to give the title compound as a pale yellow oil. PMR ($CDCl_3$): & 1.05 (6H, s), 1.52 (6H, s), 2.30 (2H, s), 3.71 (1H, s), 7.22 (1H, dd, J~8.5 Hz, 2.1 Hz), 7.28 (1H, d, J~8.5 Hz), 7.35 (1H, d, J~2.1 Hz)

Using ethyl magnesium bromide, instead of methyl magnesium bromide, provides the corresponding 4-bromo-2-(1,1 dimethyl 3-ethyl-3-hydroxypentyl)-thiophenol.

2,2,4,4-Tetramethyl-6-bromothiochroman (Compound 72)

A mixture of 500 mg (1.49 mmol) of 4-bromo-2-(1,1,3-trimethyl-3-hydroxybutyl) thiophenol (Compound 71) and 8 ml of 20 percent aqueous $H_2SO_4$ was heated at reflux for 24 h. The mixture was extracted with hexanes, the organic extracts were combined washed successively with water, saturated $NaHCO_3$, water again, saturated NaCl and then dried ($MgSO_4$). The solvent was removed in vacuo and the residue purified by flash chromatography (silica; hexanes) to give the title compound as a colorless oil. PMR ($CDCl_3$): & 1.35 (6H, s), 1.40 (6H, s), 1.93 (2H, s), 7.17 (1H, dd, J~8.4 Hz, 2.1 Hz), 7.23 (1H, d, J~8.4 Hz), 7.26 (1H, d, J~2.1 Hz). MS exact mass, m/e 284.0221 (calcd. for $C_{13}H_{17}S\,Br$, 284.0234).

2,2,4,4-Tetramethyl-6-trimethylsilylethynyl-thiochroman (Compound 73)

A solution of 600 mg (2.11 mmol) of 2,2,4,4-tetramethyl-6-bromothiochroman (Compound 72) in 1.5 of triethylamine was placed in a heavy-walled tube and degassed and then treated under argon with 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloride. The reaction mixture was degassed again, then placed under argon and the tube was sealed. The mixture was heated at 100 degrees C. for 24 h, allowed to cool to room temperature and then treated with a further 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloride. The mixture was then degassed, placed under argon and then heated in the sealed tube at 100 degrees C. for 96 h. The mixture was cooled to room temperature and extracted with $3 \times 10$ ml of ether. The organic extracts were combined, washed successively with 25 ml of water and 25 ml of saturated sodium chloride solution and then dried ($MgSO_4$). The solvent was removed in vacuo and the residue purified by flash chromatography (silica; hexanes followed by 3% ethyl acetate in hexanes) to give the title compound as a yellow, crystalline solid. PMR ($CDCl_3$): & 0.23 (9H, s), 1.36 (6H, s), 1.39 (6H, s), 1.94 (2H, s), 7.17 (1H, dd, J~8.2 Hz, 1.8 Hz), 7.25 (1H, d, J~1.8 Hz), 7.30 (1H, d, J~8.2 Hz). MS exact mass, m/l 302.1519 (calcd. for $C_{18}H_{26}\,S\,Si$, 382.1524).

2,2,4-Tetramethyl-6-ethynylthiochroman (Compound 3)

To a solution of 527.6 mg (1.75 mmol) of 2,2,4,4-tetramethyl-6-trimethylsilyl-ethynylthiochroman (Compound 73) in 4 ml of isopropanol was added, under argon, 4 ml of 1N KOH solution. The reaction mixture was stirred at room temperature for 20 h and the isopropanol was then removed under vacuum. The residue was extracted with ether and the combined ether extracts were washed successively with water and saturated NaCl solution and then dried ($MgSO_4$). The solvent was removed in vacuo to give the title compound as a yellow oil. PMR ($CDCl_3$): & 1.34 (6H, s), 1.37 (6H, s), 1.91 (2H, s), 2.99 (1H, s), 7.17 (1H, dd, J~8.1 Hz, 1.8 Hz), 7.26 (1H, d, J~1.8 Hz), 7.30 (1H, d, J~8.1 Hz). MS exact mass, m/e 230.1122 (calcd. for $C_{15}H_{18}S$, 230.1129)

Diphenyl-3-methyl-3-buten-1-yl phosphate (Compound 75)

To an ice-cooled solution of 12.2 g (141.65 mmol) of 3-methyl-3-buten-1-ol (Aldrich) and 11.9 g (150.44 mmol) of pyridine in 100 ml of tetrahydrofuran was added dropwise under argon a solution of 38.5 g (143.21 mmol) of diphenyl chlorophosphate (Compound 32) in 100 ml of tetrahydrofuran. The mixture was heated at reflux for 3 hours and then cooled and filtered. The filtrate was concentrated in vacuo and the residue dissolved in 400 ml of 1:1 ether and hexane and then washed with $2 \times 200$ ml water, 75 ml saturated NaCl solution and dried ($MgSO_4$). The solvent was removed in vacuo to give the title compound as a pale yellow oil. PMR ($CDCl_3$): & 1.69 (3H, s), 2.37 (2H, t, J~7 Hz), 4.32 (2H, q, J~7 Hz), 4.72 (1H, s), 4.80 (1H), 7.10–7.35 (10H, m). 4,4-Dimethylchroman (Compound 76)

To a dry, ice-cooled flask containing 34.95 g (0.134 mol) of stannic chloride was added quickly under argon 63.0 g (0.669 mol) of phenol. The mixture was stirred at 0 degrees C. for 0.5 hour and then treated with 43.0 g (0.135 mol) of diphenyl-3-methyl-3-buten-1-yl phosphate (Compound 75), followed by a 5 ml carbon disulfide rinse. The mixture was at room temperature for 21 hours and then quenched by pouring onto 700 g ice and 1 liter of 1.5N NaOH. The mixture was extracted with $1 \times 600$ ml and $2 \times 300$ ml ether. The combined ether fractions were washed with 2N NaOH, saturated NaCl and dried ($MgSO_4$). Solvent was removed in vacuo and the residue purified by flash chromatography (silica; 2% ether in hexane) to give the title compound as a colorless oil. PMR ($CDCl_3$): & 1.34 (6H), 1.80–1.85 (2H, m), 4.15–4.20 (2H, m), 6.80 (1H, dd, J~8.1 Hz, 1.5 Hz), 6.87 (1H, td, J~8.1 Hz, 1.5 Hz), 7.07 (1H, td, J~8.1 Hz, 1.5 Hz), 7.26 (1H, dd, J~8.1 Hz, 1.5 H).

In a similar manner, but substituting the corresponding 3 alkylphenol for phenol, there may be prepared the following compounds:
4,4,7-trimethylchroman;
4,4-dimethyl-7-ethylchroman;
4,4-dimethyl-7-propylchroman; and
4,4-dimethyl-7-pentylchroman.

4,4-Dimethyl-6-acetylchroman (Compound 77)

To a stirred solution of 7.94 g (48.9425 mmol) of 4,4-dimethylchroman (Compound 76) in 70 ml of nitromethane was added under argon 4.0 g (50.96 mmol) of acetyl chloride followed by 6.8 g (51 mmol) of aluminum chloride. This was stirred at room temperature for 5.5 hours and then cooled in an ice bath and treated slowly with 70 ml of 6N hydrogen chloride. The resultant mixture was stirred at room temperature for 10 minutes and then treated with 100 ml ether and the organic layer separated. The organic layer was washed with water, saturated $NaHCO_3$ and saturated NaCL solutions and dried ($MgSO_4$). Solvent was removed in vacuo and the residue by flash chromatography (silica; 10% ethyl acetate in hexanes). This was followed by kugelrohr distillation (95-100 degrees C.; 0.15 mm) to give the title compound as a colorless oil. PMR ($CDCl_3$): & 1.40 (6H), 1.95-2.00 (2H, m), 2.58 (3H), 4.25-4.30 (2H, m), 6.83 (1H, d, J~8.0 Hz), 7.62 (1H, dd, J~8.0 Hz, 1.5 Hz), 8.00 (1H, d, J~1.5 Hz).

Proceeding in the same manner, the other chroman compounds, made similar to Compound 76, are converted to their respective acetyl analogs.

4,4-Dimethyl-6-ethynylchroman (Compound 4)

To a solution of 2.47 g (24.41 mmol) of diisopropylamine in 40 ml dry tetrahydrofuran under argon at −78 degrees C. was added dropwise 15.2 ml of 1.6M (24.32 mmol) n-butyl lithium in hexane. This mixture was stirred at −78 degrees C. for 1 hour and then treated dropwise with a solution of 4.98g (24.38 mmol) of 4,4-dimethyl-6-acetylchroman (Compound 77) in 1 ml of tetrahydrofuran. After stirring at −78 degrees C. for 1 hour, the solution was treated with 4.2 g (24.36 mmol) of diethyl chlorophosphate. The cooling bath was then removed and the reaction mixture stirred at room temperature for 2.75 hours. This solution was then transferred using a double ended needle to a solution of lithium diisopropyl amide [prepared using 4.95 g (48.92 mmol) of diisopropylamine and 30.5 ml of 1.6M (48.8 mmol) n-butyllithium in hexane] in 80 ml tetrahydrofuran at −78 degrees C. The cooling bath was removed and mixture stirred at room temperature for 18 hours and then quenched with 50 ml water and 25 ml of 3N hydrogen chloride. The mixture was extracted with 2×100 ml and 3×50 ml of pentane and the combined organic fractions washed with 3N hydrogen chloride, water, saturated $NaHCO_3$ and saturated NaCl solutions and then dried ($MgSO_4$). Solvent was then removed in vacuo and the residue purified by flash chromatography (silica; 10% ethyl acetate in hexane) followed by kugelrohr distillation (70 degrees C.; 0.35 mm) to give the title compound as a colorless crystalline solid. PMR ($CDCl_3$): & 1.33 (6H), 1.81-1.86 (2H, m), 3.00 (1H, s), 4.19-4.24 (2H, m), 6.75 (1H, d, J~8.5 Hz), 7.22 (1H, dd, J~8.5 Hz, 2.3 Hz), 7.44 (1H, d, J~2.3 Hz).

Using this method, the acetyl derivatives, made similar to Compound 77, are converted to the ethynyl form.

4,4-dimethyl-6-ethynylchroman ZnCl (Compound 79) and ethyl 4-(4,4-dimethylchroman-6-yl-ethynyl) benzoate (Compound 80)

Reaction vessels used in this procedure were flame dried under vacuum and all operations were carried out in an oxygen-free, argon or nitrogen atmosphere. To a solution of 509.4 mg (2.74 mmol) of 4,4-dimethyl-6-ethynyl chroman (Compound 78) in 4 ml of dry tetrahydrofuran at 0 degrees C. was added dropwise 1.72 ml of 1.6M (2.75 mmol) of n-butyl lithium in hexane. Stirring was commenced at 0 degrees C. for 30 minutes and at room temperature for 15 minutes, after which the solution was cooled again to 0 degrees C. and then treated with a solution of 380 mg (2.79 mmol) of fused zinc chloride in 5 ml of dry tetrahydrofuran using a double ended needle. The resulting solution was stirred at 0 degrees C. for 1 hour and then at room temperature for 15 minutes to give Compound 79.

This product was not isolated but further used as follows: A solution of 628.6 mg (2.74 mmol) of ethyl 4-bromobenzoate in 4 ml of dry tetrahydrofuran was transferred by double ended needle into a suspension of 380 g (0.33 mmol) of tetrakistriphenylphosphine palladium in 5 ml dry tetrahydrofuran and stirred at room temperature for 15 minutes, then treated by double ended needle with the solution of alkynyl zinc chloride prepared above. The mixture was stirred at room temperature for 20 hours and then quenched with ice and 30 ml of 3N hydrogen chloride. The mixture was then extracted with 3×75 ml ether and ether extracts were combined and washed successively with saturated $NaHCO_3$ and saturated NaCl solutions and then dried ($MgSO_4$). Solvent was removed in vacuo and the residue further purified by flash chromatography (silica; 10% ethyl acetate in hexane) to obtain ethyl 4-(4,4-dimethylchroman-6-yl-ethynyl) benzoate (Compound 80) as a white solid. PMR ($CDCl_3$): & 1.36 (6H), 1.42 (3H, t, J~7.3 Hz), 1.82-1.86 (2H, m), 4.21-4.25 (2H, m), 4.40 (2H, q, J~7.3 Hz), 6.79 (1H, d, J~8.1 Hz), 7.28 (1H, dd, J~8.1 Hz, 2.2 Hz), 7.50 (1H, d, J~2.2 Hz), 7.58 (2H, d, J~8.7 Hz), 8.03 (2H, d, J~8.7 Hz).

Phenyl 3,3-dimethylacrylate (Compound 81)

To an ice bath cooled solution of 1.29 g (54 mmol) of NaH (obtained from a 60% suspension in mineral oil by 3×10 ml hexane wash) in 20 ml of dry THF was added slowly under oxygen a solution of 5 g (53 mmol) of phenol in 50 ml of dry THF. The mixture was then treated with a solution of 7 g (59 mmol) of dimethylacryloyl chloride in 30 ml of dry THF. The cooling bath was then removed and the mixture was stirred for a further 2.5 h. The reaction mixture was then poured into 150 ml of water containing 1 ml of glacial acetic acid. The mixture was extracted with 150 ml ether and the ether extract washed with saturated NaCl solution and then dried ($MgSO_4$). The solvent was removed in vacuo and the residue purified by flash chromatography (silica; 5% ether in hexanes) to give the title compound as a yellow oil. PMR ($CDCl_3$)): & 1.99 (3H, s), 2.24 (3H, s), 5.93 (1H, broad s), 7.10 (2H, d, J~7.8 Hz) 7.22 (1t, J~7.8 Hz), 7.38 (2H, t, J~7.8 Hz).

4,4-Dimethyl-2-oxo-chroman (Compound 82)

To a stirred, ice-cooled suspension of 10.4 g (78 mmol) of aluminum chloride in 160 ml of methylene chloride was added slowly under argon a solution of 7 g (39.8 mmol) of phenyl 3,3-dimethylacrylate (Compound 83) in 40 ml of methylene chloride. The cooling bath was removed and the mixture stirred for a further 42 h. The mixture was poured into a mixture of ice and brine and the organic layer separated. The aqueous layer was extracted with methylene chloride and the organic extracts were combined and washed with saturated NaCl solution and then dried ($MgSO_4$). The solvent was removed in vacuo and the residue purified by flash chromatography (silica; 10% ether in hexane) to give the title compound as a colorless oil. PMR (CDCl$_3$: & 1.30 (6H, s), 2.56 (2H, s), 7.06 (1H, dd, J~8.0 Hz, 1.4 Hz), 7.16 (1H, td, J~8.0 Hz, 1.4 Hz), 7.26 (1H, td, J~8.0 Hz, 1.7 Hz), 7.33 (1H, dd, J~8.0 Hz, 1.7 Hz). MS exact mass, m/e 176.0852 (calcd. for C$_{11}$H$_{12}$O$_2$, 176.0837.

2-(1,1,3-Trimethyl-3-hydroxybutyl)phenol (Compound 83)

To 11 ml of 3.0M (33 mmol) methyl magnesium chloride in THF, cooled in an ice bath, was added, under nitrogen, a solution of 1.96 g (11.1 mmol) of 4,4-dimethyl-2-oxo-chroman (Compound 82) in 35 ml of dry ether. The cooling bath was then removed and the mixture stirred at room temperature for 72 h. The reaction mixture was then poured onto a mixture of 100 g of ice and 3 ml of conc. H$_2$SO$_4$ and stirred until the magnesium salts were dissolved. The organic layer was separated and the aqueous layer extracted with 2×50 ml of ether. The organic layers were combined and washed successively with water, saturated NaHCO$_3$ and saturated NaCl solutions and then dried (MgSO$_4$). The solvent was removed in vacuo and the residue was purified by flash chromatography (silica; 20% ethyl acetate in hexanes) to give the title compound as a pale yellow solid. PMR (CDCl$_3$): & 1.13 (6H, s), 1.48 (6H, s), 1.89 (1H, s), 2.23 (2H, s), 6.60 (1H, dd, J~7.9 Hz, 1.4 Hz), 6.83 (1H, s), 6.84 (1H, td, J~7.9 Hz, 1.4 Hz), 7.07 (1H, td, J~7.9 Hz, 1.6 Hz), 7.31 (1H, dd, J~7.9 Hz, 1.6 Hz). MS exact mass, m/l 20.1458 (calcd. for C$_{13}$H$_{20}$O$_2$, 208.1464).

2,2,4,4-Tetramethyl-chroman (Compound 84)

A mixture of 2.98 g (14.3 mmol) of 2-(1,1,3-trimethyl-3-hydroxybutyl) phenol (Compound 83) and 40 ml of 20% aqueous H$_2$SO$_4$ was heated at reflux, under nitrogen, for 4 h. The mixture was stirred at room temperature for a further 72 h and then diluted with 50 ml of water. The mixture was extracted with 3×20 ml of hexanes. The organic extracts were then combined and washed successively with water and saturated NaCl solution and then dried (MgSO$_4$). The solvent was then removed in vacuo to give the title compound as a colorless oil. PMR (CDCl$_3$): & 1.36 (6H, s), 1.37 (6H, s), 1.83 (2H, s), 6.71 (1H, dd, J~8.2 Hz, 1.5 Hz) 6.92 (1H, td, J~8.2 Hz, 1.5 Hz), 7.09 (1H, td, J~8.2 Hz, 1.5 Hz), 7.29 (1H, dd, J~8.2 Hz, 1.5 Hz).

2,2,4,4-Tetramethyl-6-acetyl-chroman (Compound 85)

To an ice bath cooled solution of 2 g (10.53 mmol) of 2,2,4,4-tetramethylchroman (Compound 84) in 25 ml of nitromethane was added, under nitrogen, 941 mg (11.99 mmol) of acetyl chloride followed by 1.59 g (11.92 mmol) of aluminum chloride. The cooling bath was then removed and the mixture stirred at room temperature for 16 h. The mixture was then cooled again in an ice bath and treated with 25 ml of conc. HCl. The mixture was then filtered and the residue washed with methylene chloride. The filtrate was concentrated in vacuo and the resultant residue was purified by flash chromatography (silica; 10% ethyl acetate in hexanes) to give the title compound as a yellow oil. PMR (CDCl$_3$): & 1.38 (6H, s), 1.39 (6H, s) 1.87 (2H, s), 2.56 (3H, s), 6.83 (1H, d, J~8.7 Hz), 7.71 (1H, dd, J~8.7 Hz, 2.1 Hz), 7.98 (1H, d, J~2.1 Hz). MS exact mass, m/e 232.1468 (calcd. for C$_{13}$H$_{20}$O$_2$, 232.1464).

2,2,4,4-Tetramethyl-6-ethynyl-chroman (Compound 5)

To a cooled (−78 degrees C.) solution of 522 mg (5.17 mmol) of diisopropylamine in 8 ml of dry THF was added slowly, under nitrogen, 3.23 ml of 1.6M (5.17 mmol) n-butyl lithium in hexane. The mixture was stirred at −78 degrees C. for 40 minutes and then treated with a solution of 1.24 g (5.17 mmol) 2,2,4,4-tetramethyl-6-acetylchroman (Compound 85) in 2 ml of dry THF. The mixture was stirred at −78 degrees C. for a further 1 h and then treated with 895 mg (5.19 mmol) of diethylchlorophosphate. The reaction mixture was allowed to warm to room temperature and transferred by double-ended needle into a solution of lithium diisopropylamide in THF at −78 degrees C. [prepared as described above from 1.04 g (10.34 mmol) of diisopropylamine and 6.46 ml of 1.6M (10.34 mmol) n-butyl lithium in hexane]. The cooling bath was removed and the mixture was stirred at room temperature for 16 h. The mixture was then treated with 10 ml of ice water and acidified to a pH of 2 with 10% HCl. The organic layer was separated and the aqueous layer was extracted with 3×30 ml of pentane. The organic extracts were combined and washed successively with 2.30 ml of dilute HCl, water, 3×30 ml of saturated NaHCO$_3$ solution and saturated NaCl solution and then dried (MgSO$_4$). The solvent was removed in vacuo and the residue was purified by flash chromatography (silica; 2% ethyl acetate in hexane) to give the title compound as a pale yellow oil. PMR (CDCl$_3$): & 1.31 (6H, s), 1.32 (6H, s), 1.50 (2H, s), 3.00 (1H, s), 6.72 (1H, d, J~8.4 Hz), 7.20 (1H, dd, J~8.4 Hz, 2.1 Hz), 7.42 (1H, d, J~2.1 Hz). MS exact mass, m/e 214.1251 (calcd. for C$_{15}$H$_{18}$O, 214.1357).

3-Methyl-phenyl-3,3-dimethylacrylate (Compound 87)

A 60% suspension of sodium hydride (3.22 g; 81 mmol) in mineral oil was washed with 3×10 ml of hexane and then treated with 30 ml of dry THF. This mixture was cooled in an ice-bath then treated with a solution of 8.6 g (79.5 mmol) of m-cresol in 80 ml of dry THF. The reaction mixture was stirred for 10 min and then treated with a solution of 10.5 g (88.5 mmol) of dimethylacryloyl chloride in 40 ml of dry THF. The reaction mixture was stirred at room temperature for 96 h and then poured into a mixture of 150 ml of water and 1 ml of glacial acetic acid. The mixture was stirred for 10 min and the organic layer was separated. The aqueous layer was extracted with 2×50 ml of ether. The organic layers were combined and washed successively with water and saturated NaCl solution and then dried (MgSO$_4$). The solvent was removed in vacuo and the residue was purified by flash chromatography (silica; 10% ethyl acetate in hexane) to give the title compound as a pale yellow Oil. PMR (CDCl$_3$): & 1.95 (3H, d, J~1.3 Hz), 2.21 (3H, d, J~1.2 Hz), 2.34 (3H, s), 5.90 (1H, broad S), 6.86–6.93 (2H, m), 7.01 (1H, d, J~7.2 Hz), 7.24 (1H, t, J~7.2 Hz).

2-(1,1,3-Trimethyl-3-hydroxybutyl) 5-methyl-phenol (Compound 88)

To an ice-bath cooled suspension of 13 g (97.5 mmol) of aluminum chloride in 200 ml of methylene chloride was added dropwise under argon a solution of 9.0 g (47.4 mmol) of 3-metyl-phenyl-3,3-dimethylacrylate (Compound 87) in 100 ml of methylene chloride. The reaction mixture was stirred at 0 degrees C. for a further 30 min and then at room temperature for 15 h. The reaction mixture was poured into 200 ml of an ice water/salt mixture and the organic layer was separated. The aqueous layer was extracted with 50 ml of ether. The organic layers were combined and washed successively with water and saturated NaCl solution and then dried (MgSO$_4$). The solvent was removed in vacuo and the residue purified by flash chromatography (silica; 5% ethyl acetate in hexane) to give an approximately 2.5:1 mixture of isomeric products, 4,4,7-trimethyl-2-oxo-chroman and 4,4,5-trimethyl-2-oxo-chroman as a pale yellow oil. To a solution of 3.8 g (20 mmol) of this mixture of isomeric 2-oxo-chromans in 60 ml of ether at 0 degrees C. was added under argon 20 ml of 3.0M (60 mmol) of methyl magnesium bromide in ether. The reaction mixture was stirred at room temperature for 48 h and then poured onto a mixture of ice and 1 ml of conc. H$_2$SO$_4$. The organic layer was separated and the aqueous layer extracted with 2×50 ml of ether. The organic layers were combined and washed successively with water, saturated NaHCO$_3$ solution, water again and then saturated NcCl solution and then dried (MgSO$_4$). The solvent was removed in vacuo and the residue was purified by flash chromatography (silica; 15% ethyl acetate in hexanes) to give the title compound as a colorless oil. PMR (CDCl$_3$): & 1.14 (6H, s), 1.45 (6H, s), 2.19 (3H, s), 2.21 (2H, s), 6.39 (1H, d, J~1.8 Hz), 6.67 (1H, dd, J~7.9 Hz, 1.8 Hz), 7.16 (1H, d, J~7.9 Hz), 7.44 (1H, s).

2,2,4,4,7-Pentamethyl-chroman (Compound 89)

To 2.16 g (11.7 mmol) of 2-(1,1,3-trimethyl-3-hydroxybutyl) 5-methyl-phenol (Compound 88) was added under nitrogen 50 ml of 20% aqueous sulfuric acid. The reaction mixture was heated at reflux for 13 h and then cooled. The organic layer was separated and the aqueous layer was extracted with ether. The organic extracts were combined and washed successively with water, saturated NaHCO$_3$ solution, water again and saturated NaCl solution and then dried (MgSO$_4$). The solvent was removed in vacuo to give the title compound as a yellow oil. PMR (CDCl$_3$): & 1.32 (6H, s), 1.34 (6H, s), 1.81 (2H, s), 2.26 (3H, s), 6.63 (1H, s), 6.72 (1H, d, J~7.9 Hz), 7.15 (1H, d, J~7.9 Hz).

2,2,4,4,7-Pentamethyl-6-acetyl-chroman (Compound 90)

To an ice-bath cooled solution of 1.96 g (9.6 mmol) of 2,2,4,4,7-pentamethyl-chroman (Compound 89) in 30 ml of nitromethane was added under argon 1.059 g (13.5 mmol) of acetyl chloride followed by 1.9 g (14.3 mmol) of aluminum chloride. The reaction mixture was stirred at room temperature for 14 h then cooled in an ice-bath and treated with 25 ml of conc. HCl. The mixture was warmed to room temperature and diluted with ether and water. The organic layer was separated and the aqueous layer extracted with ether. The organic extracts were combined and washed successively with water, saturated NaHCO$_3$ solution, water again, and saturated NaCl solution, and then dried (MgSO$_4$). The solvent was removed in vacuo and the residue was purified by flash chromatography (silica; 5% ethyl acetate in hexanes) to give the title compound as a pale yellow oil. PMR (CDCl$_3$): 1.36 (6H, s), 1.37 (6H, s), 1.86 (2H, s), 2.49 (3H, s), 2.56 (3H, s), 6.65 (1H, s), 7.74 (1H, s).

2,2,4,4-Pentamethyl-6-ethynyl-chroman (Compound 9)

To a solution of 455 mg (4.5 mmol) of disopropylamine in 5 ml of dry THF at −78 degrees C. was added under argon 3 ml of 1.5M n-BuLi in hexane. The mixture was stirred at −78 degrees C. for a further 45 min and then treated with a solution of 1.07 g (4.3 mmol) of 2,2,4,4,7-pentamethyl-6-acetyl-chroman (Compound 90) in 4 ml of dry THF. The reaction mixture was stirred at −78 degrees C. for 1 h and then treated with 776 mg (4.5 mmol) of diethyl chlorophosphate. The mixture was allowed to warm to room temperature and then transferred by a double-ended needle into a solution of lithium diisopropyl amide in 10 ml dry THF at −78 degrees C. which was prepared as described above using 910 mg (9.0 mmol) of diisopropylamine and 6 ml of 1.5M (9.0 mmol) n-BuLi in hexane. The mixture was stirred at room temperature for 15 h and then poured into 10 ml of iced water. The mixture was acidified to pH=2 with 10% HCl solution. The organic layer was separated and the aqueous layer extracted with pentane. The organic extracts were combined and washed successively with water, saturated NaHCO$_3$ and saturated NaCl solutions and then dried (MgSO$_4$). The solvent was removed in vacuo and the residue purified by Kugelrohr distillation (82 degrees C., 0.3 mm) to give the title compound as a pale yellow oil. PMR (CDCl$_3$): & 1.32 (6H, s), 1.34 (6H, s), 1.81 (2H, s), 2.36 (3H, s), 3.18 (1H, s), 6.64 (1H, s), 7.40 1H (s). MS exact mass, m/e 228.1520 (calcd. for C$_{16}$H$_{20}$O, 228.1514).

N-(4-Bromophenyl)3.3-dimethylacrylamide (Compound 92)

To a solution of 9.48 g (80 mmol) of 3,3-dimethylacryloyl chloride in 200 ml of dry THF was added with vigorous shaking a solution of 13.76 g (80 mmol) of 4-bromoaniline in 300 ml of dry THF. The mixture was stood at room temperature for 2 h and then treated with 80 g of ice followed by 200 ml of hexane. The organic layer was separated and the aqueous layer was extracted with 2×50 ml of hexanes. The organic layers were combined and washed successively with 30 ml of water and 2×30 ml of saturated NaCl solution and then dried (MgSO$_4$). The solvent was removed in vacuo and the residue purified by recrystallization from an ethyl acetate and hexanes mixture to give the title compound as colorless crystals. PMR (CDCl$_3$): & 1.91 (3H, s), 2.23 (3H, s), 5.73 (1H, broad s), 7.38-7.55 (5H, m).

4,4-Dimethyl-6-bromo-2-oxo-1,2,3,4-tetrahydroquinoline (Compound 93)

To 6.7 g (26.02 mmol) of molten N-(4-bromophenyl)3,3dimethylacrylamide (Compound 92) (heated to 135 degrees C.) was added 4.15 g (31.09 of) aluminum chloride over 25 min. The reaction mixture was stirred at 130 degrees C. for 16 h and then treated with a further 1 g (7.5 mmol) of aluminum chloride. The reaction mixture was heated at 130 degrees C. for a further 9 h and then cooled to room temperature: The reaction was then quenched by the slow addition of 100 ml of ice cold water with slight warming of flask to facilitate mixing. The mixture was extracted with 1×100 ml and 4×50 ml of ether. The organic extracts were combined and washed with 25 ml of saturated NaCl solution and then dried (MgSO$_4$). The solvent was removed in vacuo and the residue purified by flash chromatography (silica; 30% ethyl acetate in hexanes) to give the title compound as a pale yellow solid. PMR (CDCl$_3$): & 1.37

(6H, s), 2.53 (2H, s), 6.85 (1H, d, J~8.4 Hz), 7.32 (1H, dd, J~8.4 Hz, 2.1 Hz), 7.43 (1H, d, J~2.1 Hz), 10.12 (1H, broad s).

4,4-Dimethyl-6-bromo-1,2,3,4-tetrahydroquinoline (Compound 94)

To 23.5 ml of 1.0M (23.5 mmol) lithium aluminum hydride in THF, heated to reflux under nitrogen, was added a solution of 4.95 g (19.48 mmol) of 4,4-dimethyl-6-bromo-2-oxo-1,2,3,4-tetrahydroquinoline (Compound 93) in 50 ml of dry THF and 100 ml of dry ether via a double-ended needle. The mixture was heated at reflux for 2 h and then cooled to room temperature. The reaction mixture was then quenched by the slow addition of 25 ml of water followed by 50 ml of 5% NaOH solution. The mixture was extracted with 2×25 ml of ether, the organic extracts were combined and washed successively with 25 ml each of water and saturated NaCl solution and then dried ($MgSO_4$). The solvent was removed in vacuo and the residue purified by flash chromatography (silica; 15% ethyl acetate in hexanes) to give the title compound as a brown oil. PMR ($CDCl_3$): & 1.27 (6H, s), 1.67-1.74 (2H, m), 3.23-3.32 (2H, m), 3.90 (1H, broad s), 6.33 (1H, d, J~8.4 Hz), 7.10 (1H, dd, J~8.4 Hz, 2.3 Hz), 7.25 (1H, d, J~2.3 Hz).

4,4-Dimethyl-6-trimethylsilylethynyl-1,2,3,4-tetrahydroquinoline (Compound 95)

A solution of 1.608 g (6.7 mmol) of 4,4-dimethyl-6-bromo-1,2,3,4-tetrahydroquinoline (Compound 94) in 1.5 ml of triethylamine in a heavy-walled tube was degassed under argon and then treated with 75 mg (0.39 mmol) of cuprous iodide and 50 mg (0.21 mmol) of bis(triphenylphosphine) palladium (II) chloride. The mixture was degassed again under argon, treated with 2.09 g (21.2 mmol) of trimethylsilylacetylene and the tube was sealed. The mixture was heated at 50 degrees C. for 48 h. After cooling to room temperature methylene chloride was added to the reaction mixture and the mixture filtered. The filtrate was concentrated in vacuo and the residue purified by flash chromatography (silica; 10% ethyl acetate in hexanes) to give the title compound as a yellow oil. PMR ($CDCl_3$): & 0.20 (9H, s), 1.20 (6H, s), 1.57-1.63 (2H, m), 3.16-3.25 (2H, m), 4.02 (1H, broad s), 6.24 (1H, d, J~8.2 Hz), 7.00 (1H, dd, J~8.2 Hz, 1.8 Hz), 7.26 (1H, d, J~1.8 Hz).

4,4-Dimethyl-6-ethynyl-1,2,3,4-tetrahydroquinoline (Compound 6).

To a solution of 569 mg (2.21 mmol) of 4,4-dimethyl-6-trimethylsilylethynyl-1,2,3,4-tetrahydroquinoline (Compound 95) in 3 ml of isopropanol was added, under argon, 1 ml of 1N aqueous KOH solution. The reaction mixture was stirred at room temperature for 36 h and the isopropanol was removed under vacuum. The residue was extracted with ether and the ether extract was washed successively with water and saturated NaCl solution and then dried ($MgSO_4$). The solvent was removed in vacuo and the residue was purified by flash chromatography (silica; 10% ethyl acetate in hexanes) to give the title as a brown oil. PMR ($CDCl_3$): & 1.26 (6H, s), 1.65-1.72 (2H, m), 2.96 (1H, s), 3.27-3.34 (2H, m), 6.34 (1H, d, J~8.3 Hz), 7.08 (1H, dd, J~8.3 Hz, 1.6 Hz), 7.33 (1H, d, J~1.6 Hz).

Ethyl-4-iodobenzoate (Compound 97)

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated $NaHCO_3$ and saturated NaCl solutions and dried ($MgSO_4$). Solvent was then removed in vacuo an the residue kugelrohr distilled (100 degrees C.; 0.55 mm) to give the title compound as a colorless oil, PMR ($CDCl_3$) & 1.42 (3H, t, J~7 Hz), 4,4 (2H, q, J~7 Hz), 7.8 (4H).

In the same manner, but substituting for 4-iodobenzoic acid the appropriate acid, the following compounds can be prepared:
ethyl 4-iodophenylacetate;
ethyl 3-(4-iodophenyl)propionate;
ethyl 4-(4-iodophenyl)butanoate; and
ethyl 5-(4-iodophenyl)pentanoate.

Ethyl 6-chloronicotinate (Compound 98)

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and the residue subjected to flash chromatography to give the title compound as a low-melting white solid. PMR ($CDCl_3$): & 1.44 (3H, t, J~6.2 Hz) 4.44 (2H, q, J~4.4 Hz), 7.44 (1H, d, H~8.1 Hz), 8.27 (1H, dd, J~8.1 Hz, 3 Hz), 9.02 (1H, d, J~3 Hz).

The foregoing procedure may be used to esterify any of other halo-substituted acids employed in the making of compounds such as:
ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate; and the corresponding chloro, or other halo, substituted pyrimidinyl or pyrazinyl analogues of such esters.

Ethyl 6-[4(4,4-dimethylthiochroman-6-yl)-ethynyl]nicotinate (Compound 99)

Reaction vessels used in this procedure were flame dried under vacuum and all operations carried out in an oxygen-free, argon or nitrogen atmosphere. To a solution of 465.7 mg (2.3019 mmol) of 4,4-dimethyl-6-ethynyl-thiochroman (Compound 1) in 4 ml of dry tetrahydrofuran at 0 degrees C. was added dropwise 1.5 ml of 1.6M (2.4 mmol) n-butyllithium in hexane. This was stirred at 0 degrees C. for 10 minutes and at room temperature for 10 minutes, cooled again to 0 degrees C. and then treated with a solution of 330 mg (2.4215 mmol) of fused $ZnCl_2$ in 4 ml dry tetrahydrofuran using a double ended needle. Thereafter the solution was stirred at 0 degrees C. for 30 minutes, then at room temperature for 10 minutes. A solution of 426.3 mg (2.2967 mmol) of ethyl 6-chloronicotinate (Compound 98) in 4 ml dry tetrahydrofuran was transferred by double ended needle into a suspension of 430 mg (0.37 mmol) of tetrakistriphenylphosphine palladium in 4 ml dry tetrahydrofuran and stirred at room temperature for 10 minutes, then treated by double ended needle with the solution the alkynyl zinc prepared above. This mixture was stirred at room temperature for 18 hours, then quenched with 100 ml water. Product was recovered by extraction with 3×75 ml ether. Ether fractions were combined and washed with saturated NaCl solutions and dried (MgSO₄). Solvent was removed in vacuo and the residue purified by flash chromatography (silica; 5% ethyl acetate in hexane) followed by HPLC (Whatman Partisil M-9 10/50; 4% ethyl acetate in hexane) to give the title compound as a white solid.

PMR (CDCl₃): & 1.36 (6H, s), 1.45 (3H, t, J~7 Hz), 1.96–2.00 (2H, m), 3.05–3.09 (2H, m), 4.45 (2H, q, J~7 Hz), 7.11 (1H, d, J~8.4 Hz), 7.29 (1H, dd, J~8.4 Hz, 2.2 Hz), 7.59 (1H, d, J~7.8 Hz), 7.66 (1H, d, J~2.2 Hz), 8.30 (1H, dd, J~7.8 Hz, 2.3 HZ), 9.22 (1H, d, J~2.3 Hz).

Alternative synthesis: Ethyl 6-[(4,4-dimethylthiochroman-6-yl)ethynyl]nicotinate (Compound 99) was also prepared as follows.

A solution of 15.4 g (76.2 mmol) of 4,4-dimethyl-6-ethynyl-thiochroman (Compound 1) and 14.0 g (75.5 mmol) of ethyl-6-chloronicotinate (Compound 98) in 35 ml of freshly distilled triethylamine was degassed and then treated under nitrogen with a finely powdered mixture of 1 g (5.25 mmol) of high purity cuprous iodide and 2 g (2.85 mmol) of bis(triphenylphosphine) palladium (II) chloride. The mixture was heated under nitrogen at 55 degrees C. for 20 hours and then cooled to room temperature. The triethylamine was then removed under vacuum and the residue was diluted with 200 ml of a 1:4 mixture of ethyl acetate and hexanes. This mixture was filtered through silica and the filtrate concentrated in vacuo. The resultant residue was purified by flash chromatography (silica gel; 15% ethyl acetate in hexanes) and recrystallized from a mixture of ethyl acetate and hexanes to give the title compound as a pale yellow solid.

Ethyl 6-[(4,4,7-trimethylthichroman-6-yl)ethynyl]nicotinate (Compound 100)

A mixture of 86 mg (0.4 mmol) of 4,4,7-trimethyl-6-ethynyl-thiochroman (Compound 2), 85 mg (0.46 mmol) of ethyl 6-chloronicotinate (Compound 98) and 0.8 ml of triethylamine was degassed under nitrogen and then treated with a mixture of 10 mg (0.05 mmol) of cuprous iodide and 20 mg (0.03 mmol) of bis(triphenylphosphine) palladium (II) chloride. The reaction mixture was heated at 55 degrees C. under a nitrogen atmosphere for 18 hours. The mixture was then extracted with 1.5 ml of 40% ethyl acetate in hexanes and purified by flash chromatography (silica; 10% ethyl acetate in hexanes) to give the title compound as a yellow solid.

PMR (CDCl₃): & 1.32 (6H, s), 1.43 (3H, t, J~7.2 Hz), 2.44 (3H, s), 3.01–3.05 (2H, m), 4.42 (2H, q, J~7.2 Hz), 6.98 (1H, s), 7.54–7.63 (2H, m), 8.27 (1H, dd, J~8.3 Hz, 2.3 Hz), 9.21 (1H, d, J~2.3 Hz).

Ethyl 6-[(4,4-dimethylchroman-6-yl)ethynyl]nicotinate (Compound 101)

Reaction vessels used in this procedure were flame dried under vacuum and all operations were carried out in an oxygen-free, argon or nitrogen atmosphere. To a solution of 509.4 mg (2.74 mmol) of 4,4-dimethyl-6-ethynylchroman (Compound 4) in 4 ml of dry tetrahydrofuran at 0 degrees C. was added dropwise 1.72 ml of 1.6M (2.75 mmol) of n-butyl lithium in hexane. Stirring was commenced at 0 degrees C. for 30 minutes and at room temperature for 15 minutes, after which the solution was cooled again to 0 degrees C. and then treated with a solution of 380 mg (2.79 mmol) of fused zinc chloride in 5 ml of dry tetrahydrofuran using a double ended needle. The resulting solution was stirred at 0 degrees C. for 1 hour and then at room temperature for 15 minutes. A solution of 628.6 mg (2.74 mmol) of ethyl 6-chloronicotinate (Compound 98) in 4 ml of dry tetrahydrofuran was transferred by double ended needle into a suspension of 380 mg (0.33 mmol) of tetrakistriphenylphosphine palladium in 5 ml dry tetrahydrofuran and the mixture was stirred at room temperature for 15 minutes and then treated by double ended needle with the solution of alkynyl zinc prepared above. The mixture was stirred at room temperature for 20 hours and then quenched with ice and 30 ml of 3N hydrogen chloride. The mixture was extracted with 3×75 ml ether and ether extracts were combined and washed successively with saturated NaHCO₃ and saturated NaCl and then dried (MgSO₄). Solvent was removed in vacuo and the residue further purified by flash chromatography (silica; 10% ethyl acetate in hexane) to give the title compound as a yellow solid.

PMR (CDCl₃): & 1.36 (6H, s), 1.44 (3H, t, J~7.1 Hz), 1.83–1.87 (2H, m), 4.22–4.26 (2H, m), 4.44 (2H, q, J-7.1 Hz), 6.80 (1H, d, J~7.6 Hz), 7.35 (1H, d, J~8.9 Hz), 7.58 (1H, d, J~7.6 Hz), 7.60 (1H, m), 8.28 (1H, d, J~8.9 Hz), 9.21 (1H, s).

Ethyl 6-[(2,2,4,4-tetramethyl-thiochroman-6-yl)-ethynyl]-nicotinate (Compound 102)

A solution of 232 mg (1.01 mmol) of 2,2,4,4-tetramethyl-6-ethynylthiochroman (Compound 3) and 190 mg (1.03 mmol) of ethyl 6-chloro-nicotinate (Compound 98) in 2 of triethylamine was placed in a heavy-walled glass tube, degassed placed under argon and then treated with a powdered mixture of 53 mg (0.28 mmol) of cuprous iodide and 84 mg (0.12 mmol) of bis(triphenylphosphine) palladium (II) chloride. The mixture was degassed again, placed under argon and the tube was sealed. The reaction mixture was heated at 55 degrees C. for 60 h and then cooled to room temperature. The mixture was treated with water and ether and the organic layer was separated rated. The aqueous layer was extracted with ether. The organic layers were then combined and washed with saturated NaCl solution and then dried (MgSO₄). The solvent was removed vacuo and the resultant residue was purified by flash chromatography (silica; 10% ethyl acetate in hexanes) to give the title compound as a dark yellow oil. PMR (CDCl₃): & 1.32–1.43 (15H, m), 1.92 (2H, s), 4.38 (2H, q, J~7.1 Hz), 7.28 (1H, dd, J~8.3 Hz, 1.8 Hz), 7.32–7.38 (2H, m), 7.53 (1H, d, J~8.3 Hz), 8.24 (1H, dd, J~8.2 Hz, 2.2 Hz), 9.16 (1H, d, J~2.2 Hz). MS exact mass, m/e 379.1594 (calcd. for C₂₃H₂₅NO₂S, 379.1606).

Ethyl 6-[(2,2,4,4-tetramethylchroman-6-yl)-ethynyl]nicotinate (Compound 103)

A solution of 233 mg (1.09 mmol) of 2,2,4,4-tetramethyl-6-ethynylchroman (Compound 5) and 209 mg (1.09 mmol) of ethyl 6chloroni cotinate (Compound 98) in 1 ml of triethylamine was degassed and then treated under argon with a powdered mixture of 50 mg (0.26 mmol) of cuprous iodide and 100 mg (0.14 mmol) of bis(triphenylphosphine) palladium (II) chloride. The reaction mixture was heated under argon at 55 degrees C. for 80 h and then cooled to room temperature. The triethylamine was then removed under vacuum and the residue purified by flash chromatography (silica; 5% ethyl acetate in hexanes) to give the title compound as a yellow oil. PMR (CDCl$_3$): & 1.36 (12H, s), 1.42 (3H, t, J~7.2 Hz), 1.85 (2H, s), 4.37 (2H, q, J~7.2 Hz), 6.79 (1H, d, J~4 Hz), 7.34 (1H, dd, J~8.4 Hz, 2.1 Hz), 7.56 (1H, d, J~8.7 Hz), 7.60 (1H, d, J~2.1 Hz), 8.27 (1H, dd, J~8.7 Hz, 2.4 Hz), 9.19 (1H, d, J~2.4 Hz). MS exact mass, m/e 363.1837 (calcd. for C$_{23}$H$_{25}$O$_3$N, 363.1834).

Ethyl-6-[(2,2,4,4,7-pentamethyl-6-chromanyl)-ethynyl]-nicotinate (Compound 104)

A solution of 300 mg (1.316 mmol) of 2,2,4,4,7-pentamethyl-6-ethynyl-chroman (Compound 9) and 245.6 mg (1.3276 mmol) of ethyl 6-chloro-nicotinate (Compound 98) in 2 ml of triethylamine was placed in a pressure tube and a stream of nitrogen was bubbled through the solution for 15 min. The tube was then flushed with argon and a finely ground mixture 100 mg (0.1425 mmol) of bis (triphenylphosphine) palladium II) chloride and 50 mg (0.2625 mmol) of cuprous iodide was added to the solution. The pressure tube was then sealed and the reaction mixture heated at 60 degrees C. for 72 h. The mixture was cooled to room temperature and the triethylamine removed under vacuum. The residue was purified by flash chromatography (silica; 10% ethyl acetate in hexane) to give the title compound as a yellow solid. PMR (CDCl$_3$): & 1.37 (6H, s), 1.38 (6H, s), 1.44 (3H, t, J~7.2 Hz), 1.85 (2H, s), 2.49 (3H, s), 4.43 (2H, q, J~7.2 Hz), 6.70 (1H, s), 7.55–7.61 (2H, m), 8.28 (1H, dd, J~8.2 Hz, 2.1 Hz), 9.22 (1H, d, J~2.1 Hz). MS exact mass, m/e 377.1982 (calcd. for C$_{24}$H$_{27}$O$_3$N, 377.1991).

Ethyl 4-[(2,2,4,4,7-pentamethylchroman-6-yl)-ethynyl]benzoate (Compound 105)

Nitrogen was bubbled for 15 min through a solution of 200 (0.877 mmol) of 2,2,4,4,7-pentamethyl-6-ethynyl-chroman (Compound 9) and 245.3 mg (0.888 mmol) of ethyl 4-iodobenzonate (Compound 97) in 2 ml of triethylamine. The mixture was then placed under an argon atmosphere and treated with a finely ground mixture of 50 mg (0.2625 mmol) of cuprous iodide and 100 mg (0.1425 mmol) of bis(triphenylphosphine) palladium (II) chloride. The reaction vessel was then fitted with a reflux condenser and the mixture was heated at 55 degrees C. under argon for 72 hours. The triethylamine was then removed under vacuum and the residue purified by flash chromatography (silica, 5% ethyl acetate in hexane) to give the title compound as a yellow oil. PMR (CDCl$_3$) : & 1.32 (12H, s), 1.37 (3H, t, J~7.0 Hz), 1.80 (2H, s) 2.40 (3H, s), 4.36 (2H, q, J~7.0 Hz), 6.66 (1H, s, 7.42 (1H, s), 7.54 (2H, d, J~8.6 Hz), 7.99 (2H, d, J~8.6 Hz). MS exact mass, m/e 376.2 038 (calcd. for C$_{25}$H$_{28}$O$_3$, 376 2038).

Ethyl 4-[(2,2,4,4-tetramethylchroman-6-yl-ethynyl]benzoate (Compound 106)

A solution of 233 mg (1.088 mmol) of 2,2,4,4-tetramethyl-6-ethynyl-chroman (Compound 9) and 308 mg (1.087 mmol) of ethyl 4-iodo-benzoate (Compound 97) in 1 ml of triethylamine placed in a heavy-walled tube and degassed under argon. The mixture was treated with a fineyl ground mixture of 50 mg (0.263 mmol) of cuprous iodide and 100 mg (0.142 mmol) of bis (triphenylphosphine) palladium (II) chloride and the tube was then sealed. The reaction mixture was then heated at 55 degrees C. for 48 hours. The triethylamine was removed in vacuo and the residue was purified by flash chromatography (silica, 5% ethyl acetate in hexans) to give the title compound as yellow oil. PMR (CDCl$_3$) : & 1.33 (6H, s), 1.34 (6H, s), 1.37 (3H, t, J~7.2 Hz), 1.83 (2H, s), 4.35 (2H, q, J~7.2 Hz), 6.75 (1H, d, J~8.4 Hz), 7.24 (1H, dd, J~8.4 Hz, 2.1 Hz), 7.46 (1H, d, J~2.1 Hz), 7.54 (2H, d, J~8.1 Hz), 7.99 (2H, d, J~8.1 Hz) MS exact mass, m/e 362.1880 (calcd. for C$_{24}$H$_{26}$O$_3$, 362.1881).

4-[(2,2,4,4-tetramethyl-thiochroman-6-yl)-ethynyl]benzoate (Compound 107)

A solution of 110.7 mg (0.481 mmol) of 2,2,4,4-tetramethyl-6-ethynylthiochroman (Compound 3) and 142.3 mg (0.516 mmol) of ethyl 4-iodobenzoate (compound 97) in 2 ml of triethylamine was placed in a heavy walled glass tube and degassed under argon. The mixture was then treated with a finely ground mixture of 42 mg (0.221 mmol) of cuprous iodide and 63 mg (0.09 mmol) of bis (triphenylphosphine) palladium (II) chloride. The reaction mixture was degassed under argon again and the tube was sealed. The mixture was stirred at room temperature for 40 hours. The triethylamine was removed under vacuum and the residue purified by flash chromatography (silica, 3% ethyl acetate in hexanes) to give the title compound as a pale yellow solid. PMR (CDCl$_3$) : & 1.37–1.42 (15H, m), 1.96 (2H, s), 4.38 (2H, q, J~7.0 Hz), 7.25 (1H, dd, J~8.2 Hz, 1.8 Hz), 7.33 (1H, d, J~1.8 Hz), 7.37 (1H, d, J~8.2 Hz), 7.65 (2H, d, J~8.6 Hz), 8.01 (2H, d, J~8.6 Hz). MS exact mass, m/e 378.1636 (calcd. for C$_{24}$H$_{26}$O$_2$S, 378.165.3).

Ethyl 4-(4,4-dimethyl-1,2,3,4-tetrahydroquinolin-6-yl)ethynyl]benzoate (Compound 108)

Nitrogen gas was bubbled for 15 minutes through a solution of 145 mg (0.7838 mmol) of 4,4-dimethyl-6-ethynyl-1,2,3,4-tetrahydroquinoline (Compound 6) and 220 mg (0.797 mmol) of ethyl 4-iodobenzoate (Compound 97) in 2 ml of triethylamine placed in a heavy-walled tube. The solution was then treated with a finely ground mixture of 31 mg (0.163 mmol) of cuprous iodide and 62 mg (0.088 mmol) of bis (triphenylphosphine) palladium (II) chloride. The tube was then flushed with argon and sealed. The reaction mixture was heated at 55 degrees C. for 72 h. The mixture was allowed to cool and then treated with 1 ml of triethylamine. The mixture was further treated with a ground mixture of 15 mg (0.079 mmol) cuprous iodide and 30 mg (0.003 mmol) of bis(triphenylphosphine) palladium (II) chloride. The tube was flushed with argon and sealed and the mixture was heated at 55 degrees C. for a further 24 h. The mixture was cooled and treated with ether and water and the organic layer was separated. The aqueous layer was extracted with ether and the combined organic extracts were washed successively with water saturated NaCl solution and then dried (MgSO$_4$). The solvent was removed in-vacuo and the residue was purified by flash chromatography (silica; 10% ethyl acetate in hexane) to give the title compound as a yellow oil. PMR (CDCl$_3$) : & 1.31 (6H, s), 1.40 (3H, t, J~7.2 Hz), 1.68–1.78 (2H, m), 3.32–3.40 (2H, m), 4.17 (1H, broad s), 4.38 (2H, q, J~7.2 Hz), 6.41 (1H, d, J~8.2 Hz), 7.15 (1H, dd, J~8.2 Hz, 1.9 Hz), 7.39 (1H, d, J~1.9 Hz), 7.54 (2H, d, J~8.4 Hz), 8.00 (2H, d, J~8.4 Hz). MS exact mass, m/e 333.1729 (calcd. for C$_{22}$H$_{23}$O$_2$N, 333.1728).

Several modifications of the above described compounds and processes, and application of the herein disclosed processes to numerous compounds beyond the specific examples set forth above, may be practiced by those skilled in the art without departing from the scope and spirit of the present invention. Therefore, the scope of the present invention should be interpreted solely from the following claims, as such claims are read in light of the present disclosure.

What is claimed is:

1. Compounds of the formula,

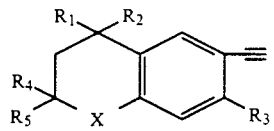

wherein
X is O and
$R_1, R_2, R_3, R_4$ and $R_5$ are hydrogen or lower alkyl having to 6 carbons, or salts of the compounds of the formula defined herein.

2. Compounds of claim 1 wherein $R_4$ and $R_5$ both are hydrogen.

3. Compounds of claim 1 wherein $R_1$ and $R_2$ both are methyl.

4. The compound of claim 3 wherein $R_3$ is methyl.

5. The compound of claim 3 wherein $R_3$ is hydrogen.

6. Compounds of claim 1 wherein $R_4$ and $R_5$ both are methyl.

7. Compounds of claim 6 wherein $R_1$ and $R_2$ both are methyl.

8. The compound of claim 7 wherein $R_3$ is methyl.

9. The compound of claim 7 wherein $R_3$ is hydrogen.

* * * * *

UNITED STATES PATENT AND TRADEMARK OFFICE
CERTIFICATE OF CORRECTION

PATENT NO. : 5,053,523    Page 1 of 4
DATED : October 1, 1991
INVENTOR(S) : Roshantha A.S. Chandraratna It is certified that error appears in the above-identified patent and that said Letters Patent is hereby corrected as shown below:

Column 3, line 61, delete the "o" and insert in its place —of the—;
Column 4, line 37, change "$R_i$" to —$R_1$—;
Column 7, line 20, after "methyl" insert — - — before the "2";
Column 7, line 29, change "scheme" to —Scheme—;
Column 7, line 30, change "With" to —with—;
Column 8, line 47, change "scheme" to—Scheme—;
Column 9, line 25, after "bis" change ")" to —(—;
Column 9, line 33, after "-" (first occurrence), delete —thiochromanyl—;
Column 9, line 35, change "(compound)" to —(Compound)—;
Column 10, line 30, change "scheme" to —Scheme—;
Column 11, line 13, change "(compound)" to —(Compound)—;
Column 11, line 20, at the end of the line, delete "thiochromane";
Column 13, line 7, after "employed" insert —.—;
Column 13, line 12, change "(compound)" to —(Compound)—;
Column 13, line 13, change "(compound)" to —(Compound)—;
Column 13, line 65, change "scheme" to —Scheme—;
Column 14, line 53, "phenyl" should be —phenol—;
Column 14, line 65, change "3is" to —38 is—;
Column 16, line 60, change "analog" to —analogous—;
Column 16, line 65, change "I Where" to —1 where—;
Column 17, line 44, after "Ethyl" insert — - — before the "4";
Column 18, line 38, after "protected" insert —or—;

UNITED STATES PATENT AND TRADEMARK OFFICE
CERTIFICATE OF CORRECTION

PATENT NO. : 5,053,523
DATED : October 1, 1991
INVENTOR(S) : Roshantha A.S. Chandraratna It is certified that error appears in the above-identified patent and that said Letters Patent is hereby corrected as shown below:

Column 18, line 39, after "other" insert —group—;

Column 18, line 67, after "the" insert —presence—;

Column 19, line 49, change "7..3" to —7.3—;

Column 20, line 67, after "used" insert —as—;

Column 20, line 68, delete "iodobenzoate" (second occurrence);

Column 21, line 3, change "tetrastriphenylphosphine" to —tetrakistriphenylphosphine—;

Column 21, line 16, "(4,4-"... should be — 4-(4,4- —...;

Column 21, line 32, change "the" to —The—;

Column 21, line 33, after "cooled" insert —to—;

Column 23, line 34, after "combined" insert —and—;

Column 23, line 48, after "1.5" insert —ml—;

Column 24, line 9, "2,2,4-"... should be — 2,2,4,4- —...;

Column 24, line 43, after "(10H, m)." start a new line;

Column 25, line 13, change "NaCL" to —NaCl—;

Column 25, line 15, after "residue" insert —purified—;

Column 25, line 34, before "tetrahydrofuran" insert —dry—;

Column 25, line 42, after "80 ml" insert —dry—;

Column 26, line 53, change "(1t," to —(1H,—; insert "t"

Column 26, line 60, change "83)" to —81)—;

Column 28, line 40, after "ice-bath" insert —and—;

UNITED STATES PATENT AND TRADEMARK OFFICE
CERTIFICATE OF CORRECTION

PATENT NO. : 5,053,523

DATED : October 1, 1991

INVENTOR(S) : Roshantha A.S. Chandraratna

Page 3 of 4

It is certified that error appears in the above-identified patent and that said Letters Patent is hereby corrected as shown below:

Column 28, line 55, change "Oil" to —oil—;

Column 30, line 1, after "2,2,4,4," insert —7—;

Column 31, line 33, "50" should be —150—;

Column 31, line 61, after "title" insert —compound—;

Column 32, line 9, after "($CDCl_3$)" insert —:—;

Column 32, line 31, after "of" insert —these—;

Column 32, line 66, after "solution" insert —of—;

Column 34, line 33, after "2" insert —ml—;

Column 34, line 34, after "degassed" insert —,—;

Column 34, line 43, delete "rated";

Column 34, line 46, before "vacuo" insert —in—;

Column 34, line 60, change "6chloroni cotinate" to — 6-chloronicotinate —;

Column 35, line 4, "4 Hz)," should be —.4 Hz),—;

Column 35, line 17, after "mixture" insert —of—;

Column 35, line 18, before "II)" insert —(—;

Column 35, line 37, after "200" insert —mg.—;

Column 35, line 54, "376 2038" should be —376.2038—;

Column 35, line 62, before "placed" insert —was—;

Column 35, line 64, "fineyl" should be —finely—;

Column 36, line 11, at the beginning of the line insert "Ethyl";

Column 36, line 15, change "(compound" to —(Compound—;

UNITED STATES PATENT AND TRADEMARK OFFICE
CERTIFICATE OF CORRECTION

PATENT NO. : 5,053,523

DATED : October 1, 1991

INVENTOR(S) : Roshantha A.S. Chandraratna

It is certified that error appears in the above-identified patent and that said Letters Patent is hereby corrected as shown below:

Column 36, line 58, after "water" insert —and—;

Column 38, line 11, Claim 1, after "having" insert —1—.

Signed and Sealed this

Twenty-fifth Day of January, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,053,523

DATED : October 1, 1991

INVENTOR(S) : Roshantha A.S. Chandraratna

It is certified that error appears in the above-identified patent and that said Letters Patent is hereby corrected as shown below:

Column 2, line 51, "another)" should be --another,--;

Column 3, line 19, "Embodoments" should be --Embodiments--;

Column 5, line 8, "retionic" should be --retinoic--;

Column 5, line 9, "retionic" should be --retinoic--;

Column 5, line 10, "retionic" should be --retinoic--;

Column 5, line 12, "retionic" should be --retinoic--;

Column 5, line 23, "Retionic" should be --Retinoic--;

Column 5, line 28, "retionic" should be --retinoic--;

Column 7, line 24, "a" should be --an--;

Column 8, line 36, "Zncl" should be --ZnCl--;

Column 8, line 40, "Zncl" should be --ZnCl--;

Column 12, line 11, after "4" insert --.--;

Column 16, line 4, "$5_5$" should be --$R_5$--;

Column 17, line 49, "phenylpropinoate" should be --phenylpropionate--;

Column 18, line 64, "Zncl" should be --ZnCl--;

Column 19, line 18, "distillatin" should be --distillation--;

Column 20, line 63, "Zncl$_2$" should be --ZnCl$_2$--;

Column 22, line 29, "bromopenyl" should be --bromophenyl--;

Column 26, line 51, "(CDCl$_3$)):" should be --(CDCl$_3$):--;

Column 29, line 22, "NcCl" should be --NaCl--;

UNITED STATES PATENT AND TRADEMARK OFFICE
CERTIFICATE OF CORRECTION

PATENT NO. : 5,053,523

DATED : October 1, 1991

INVENTOR(S) : Roshantha A. S. Chandraratna

It is certified that error appears in the above-identified patent and that said Letters Patent is hereby corrected as shown below:

Column 30, lines 2 & 3, "disopropylamine" should be —diisopropylamine—;

Column 32, line 7, "an" should be —and—; and

Column 35, line 52, "s," should be —s),—.

Signed and Sealed this

Tenth Day of May, 1994

Attest:

BRUCE LEHMAN

Attesting Officer

Commissioner of Patents and Trademarks